(12) United States Patent
Klop

(10) Patent No.: US 12,064,451 B2
(45) Date of Patent: Aug. 20, 2024

(54) FECAL MICROBIOTA TRANSPLANT COMPOSITIONS AND METHODS OF MANUFACTURE

(71) Applicant: Novel Biome Solutions Inc., Chilliwack (CA)

(72) Inventor: Jason Bernard Klop, Chilliwack (CA)

(73) Assignee: Novel Biome Solutions Inc., Chilliwack (CA)

( * ) Notice: Subject to any disclaimer, the term of this patent is extended or adjusted under 35 U.S.C. 154(b) by 0 days.

(21) Appl. No.: 18/228,865

(22) Filed: Aug. 1, 2023

(65) Prior Publication Data
US 2024/0033294 A1 Feb. 1, 2024

Related U.S. Application Data

(60) Provisional application No. 63/370,034, filed on Aug. 1, 2022.

(51) Int. Cl.
| | | |
|---|---|---|
| *A61K 35/24* | (2015.01) | |
| *A61K 9/00* | (2006.01) | |
| *A61K 9/19* | (2006.01) | |

(52) U.S. Cl.
CPC ............ *A61K 35/24* (2013.01); *A61K 9/0053* (2013.01); *A61K 9/19* (2013.01)

(58) Field of Classification Search
None
See application file for complete search history.

(56) References Cited

U.S. PATENT DOCUMENTS

| | | |
|---|---|---|
| 9,649,343 B2 | 5/2017 | Sadowsky et al. |
| 9,968,638 B2 | 5/2018 | Sadowsky et al. |
| 10,022,406 B2 | 7/2018 | Borody |
| 10,881,696 B2 | 1/2021 | Henn et al. |
| 10,905,726 B2 * | 2/2021 | Jones .................... A61K 9/4816 |
| 11,202,808 B2 | 12/2021 | Adams et al. |
| 11,357,801 B2 | 6/2022 | Adams et al. |
| 2019/0328825 A1 | 10/2019 | Adams et al. |
| 2020/0188442 A1 | 6/2020 | Borody |
| 2022/0088089 A1 | 3/2022 | Adams et al. |

FOREIGN PATENT DOCUMENTS

| | | |
|---|---|---|
| WO | 2018006088 A1 | 1/2018 |
| WO | 2024026561 A2 | 2/2024 |

OTHER PUBLICATIONS

U.S. Appl. No. 18/228,896, filed Aug. 1, 2023.
U.S. Appl. No. 18/228,913, filed Aug. 1, 2023.
PCT/CA2023/051029, Aug. 1, 2023.
"Nanjing consensus on methodology of washed microbiota transplantation", Chinese Medical Journal, 2020, 2330-2332.
Biazzo, M. Deidda G., "Fecal Microbiota Transplantation as New Therapeutic Avenue for Human Diseases", Journal of Clinical Medicine, 2020, 2330-2332.
Kang, D. , et al., "Microbiota Transfer Therapy Alters Gut Ecosystem and Improves Gastrointestinal and Autism Symptoms: An Open-Label Study. Microbiome 5, 10", 2017.
Youngsster, I , et al., "Oral, Capsulized, Frozen Fecal Microbiota Transplantation for Relapsing Clostridium difficile Infection", JAMA 2014, 2014, 1772-1778.
PCT/CA2023/051029 , "International Application Serial No. PCT/CA2023/051029, International Search Report and Written Opinion mailed Mar. 8, 2024", Novel Biome Solutions Inc., 16 pages.
Zhang, F. , et al., "Microbiota transplantation: concept, methodology and strategy for its modernization", Protein Cell., vol. 9, No. 5, ISSN: 1674-800X, May 2018, pp. 462-473.
Zhang, T. , et al., "Washed microbiota transplantation vs. manual fecal microbiota transplantation: clinical findings, animal studies and in vitro screening", Protein Cell., vol. 11, No. 4, ISSN: 1674-800X, Apr. 2020, pp. 251-266.

* cited by examiner

*Primary Examiner* — Russell G Fiebig
(74) *Attorney, Agent, or Firm* — GTC Law Group PC & Affiliates

(57) ABSTRACT

Disclosures herein relate to methods of producing oral powdered compositions for fecal microbiota transplant and related methods of treatment. Procedures for producing the powdered composition may include filtering a fecal sample with a filter medium to generate a filtrate, separating particulate matter of the filtrate to obtain a first sediment and a first supernatant, repeatedly resuspending the first sediment and separating particulate matter of the resuspended first sediment to obtain a second sediment and a second supernatant, diluting the second supernatant and repeatedly separating particulate matter out of the second supernatant to obtain a third sediment and a third supernatant, resuspending the third sediment in a cryoprotectant to obtain a mixture, and freeze-drying the mixture to obtain a freeze-dried, powdered composition, wherein the powdered composition may be substantially tasteless, odorless, and colorless.

38 Claims, 9 Drawing Sheets

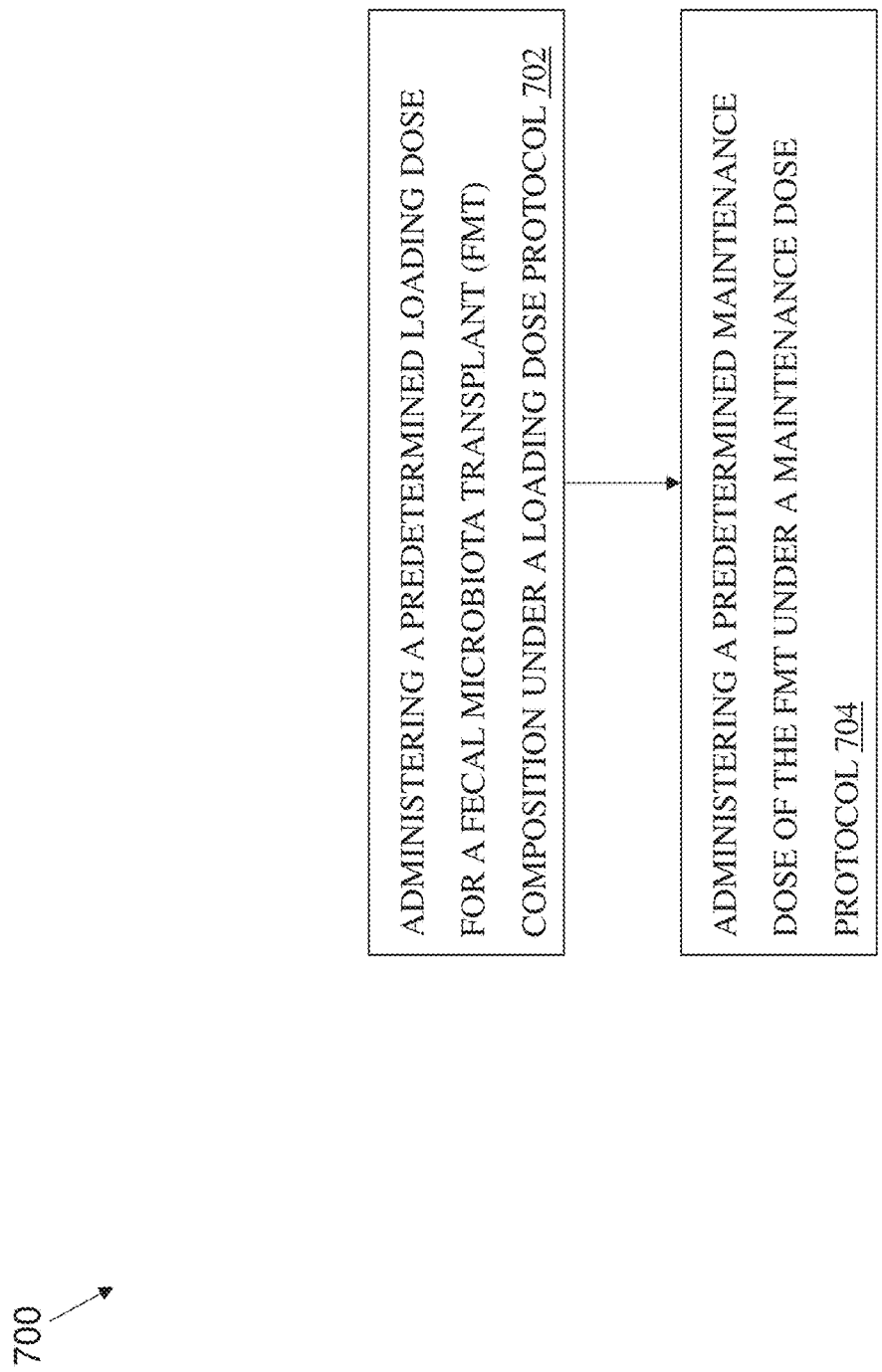

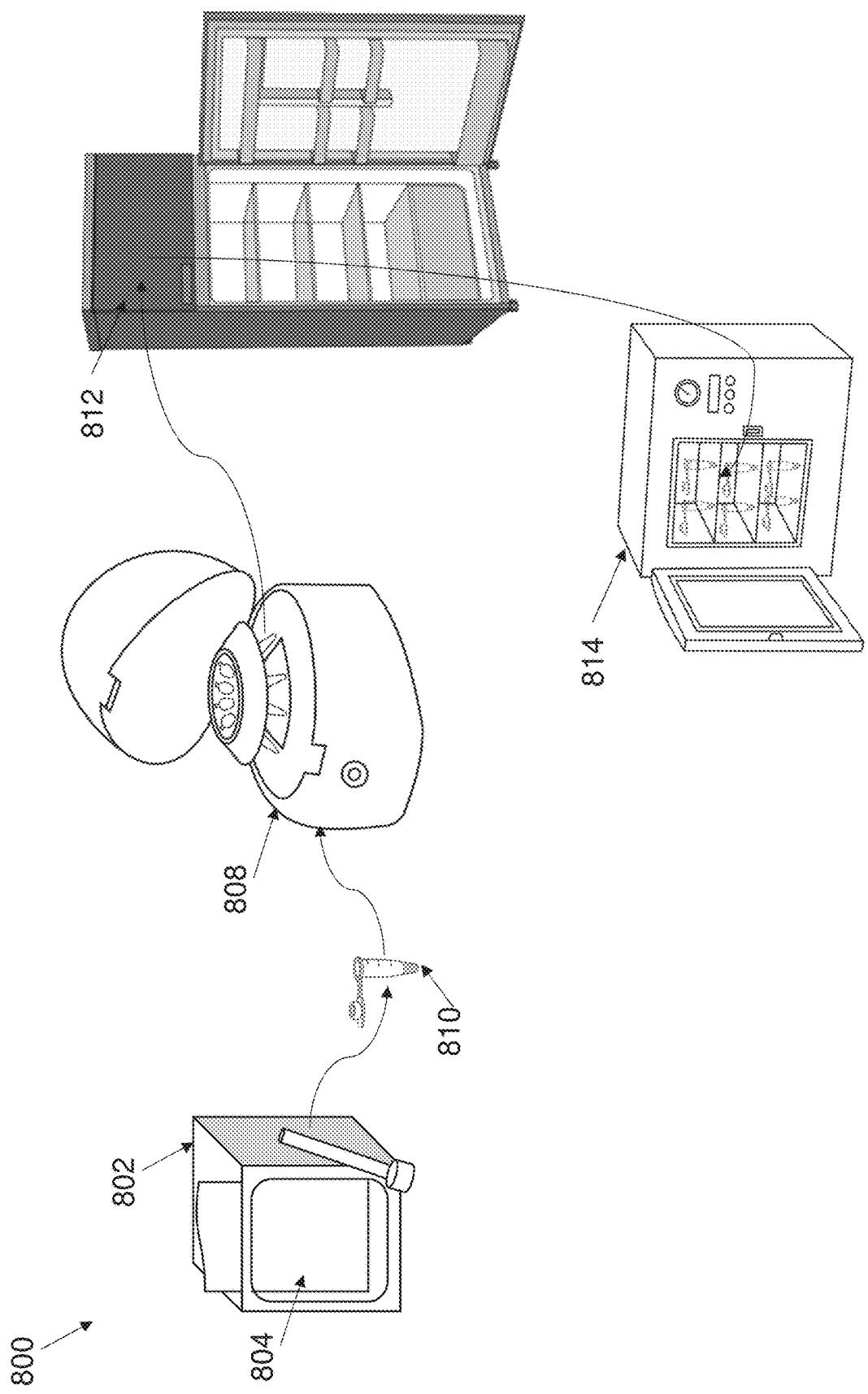

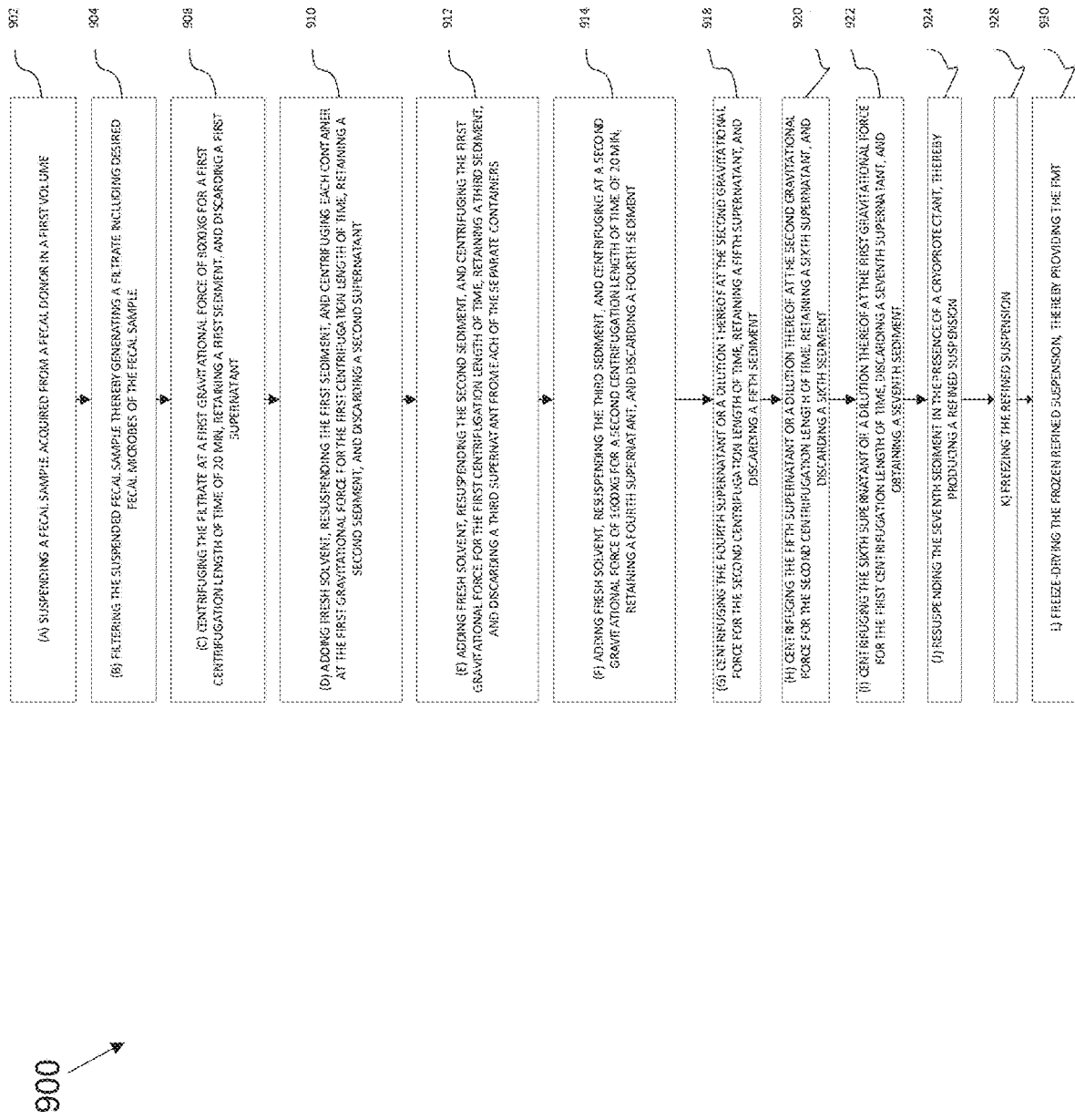

FECAL MICROBIOTA TRANSPLANT COMPOSITIONS AND METHODS OF MANUFACTURE

CLAIM TO PRIORITY

This application claims the benefit of priority to U.S. Provisional Application 63/370,034, filed Aug. 1, 2022. The foregoing application is incorporated herein by reference in its entirety for all purposes.

BACKGROUND

Field

The present disclosure relates to fecal microbiota transplant compositions and methods for treating patients.

Description of the Related Art

The presence of normal, healthy, intestinal microbiota may offer protection against various illnesses, such as *C. difficile* infections. Conversely, dysbiotic gut microbiomes may be linked to certain disorders and pathologies, such as autism spectrum disorder and recurrent *C. difficile* infections. Fecal Microbiota Transplant (FMT) provides a pathway to the restoration of a healthy gut. Encapsulated FMT compositions have been developed, however, there are challenges associated with providing FMT therapy to patients who are unable to swallow capsules and/or who do not want or cannot access the treatment by other established treatment methods (e.g., capsule, enema, endoscopy, colonoscopy, NJ-tube, etc.). Thus, there remains a need for an orally dosed FMT composition that is virtually colorless, odorless, and tasteless.

Efforts have been made to provide odorless and tasteless FMT compositions for oral delivery, but none have been successful at adequately suppressing odor and taste of fecal matter components to allow adequate compliance for administration protocols that require significant loading doses. Specifically, it is known that various filtration techniques are used as one means of attempting to isolate fecal matter microbes, but those techniques have not successfully achieved compliance with oral loading dose administration.

Another means involves culturing and growing the microbes in a separate and clean environment, but with given technologies and the amount and variety of microbes needed for a successful loading dose and engraftment, this is extremely cost prohibitive and, to date has not been proven to be as successful. Of course, it would be ideal to have a pristine source of desired fecal microbes that have never encountered actual fecal matter for the purpose of oral delivery, but this is a solution that is not remotely close to having a reasonable cost basis or proven successful for use in therapeutic protocols that require dosing with billions or trillions of microbes.

To the best of the inventor's knowledge, the state of the art as reflected in review articles relating to FMT at the time of filing this patent application showed that oral delivery of FMT was only practically achievable in encapsulated form. In other words, at the time of filing this patent application, the state of the art for oral delivery of FMT requires encapsulation, such as to provide a physical barrier between the FMT composition itself and the subject's tongue and stomach, to provide protection against thermal stress, to provide a moisture barrier during storage, to provide protection for labile components, and the like. This provides meaningful limitations to compliance, because many individuals are unable to swallow capsules without significant effort.

Other approaches to administering foul-tasting and/or foul-smelling therapeutics can be applicable to oral delivery of FMT, including masking flavor and odor (e.g., co-delivery with chocolate milk). Those approaches make more sense in circumstances where the underlying therapeutic is itself the source of the foul taste and/or smell. In this case, however, it is believed that the desirable gut microbes themselves are not responsible for the foul taste and/or smell associated with their potential oral delivery, so the entities that are responsible for said taste and/or smell might be capable of being diminished while retaining adequate quantity and quality of desired gut microbes. Applicant is aware that such flavor- and odor-masking agents have been used with compositions that purport to be useful for the delivery of gut microbes. Applicant submits that the majority of practitioners in the field would presume that an assertion that a composition is odorless and/or flavorless does not have merit if the composition is only administered with flavor- and/or odor-masking agents and there are no other test results showing lack of odor or flavor.

A need exists for orally deliverable FMT compositions that facilitate administrative protocols delivering significant quantities of desirable gut microbes.

SUMMARY

Provided herein are FMT compositions used for oral dosing that are virtually colorless, tasteless, and odorless, and related methods for manufacturing FMT compositions are disclosed. The disclosed compositions provide a dosing mechanism for patients who are unable to swallow capsules and/or who do not want or cannot access the treatment by other established treatment methods (e.g., capsule, enema, endoscopy, colonoscopy, nasogastric tube, nasoenteric tube, nasal jejunal tube, etc.), and may be useful in the treatment of colitis, Crohn's, Parkinson's, Alzheimer's, post-cancer, chronic digestive issues, gastrointestinal issues (such as those associated with long Covid), autism spectrum disorder, and the like.

Manufacturing an FMT composition may include filtering a fecal sample, purifying the fecal sample by repeated separation and resuspension of the sediment and/or the supernatant to obtain a mixture, and freeze-drying the mixture to obtain a freeze-dried, powdered composition, wherein the powdered composition may be substantially tasteless, odorless, and colorless.

An example process includes filtering a fecal sample with a filter medium to generate a filtrate, separating particulate matter of the filtrate to obtain a first sediment and a first supernatant, repeatedly resuspending the first sediment and separating particulate matter of the resuspended first sediment to obtain a second sediment and a second supernatant, diluting the second supernatant and repeatedly separating particulate matter out of the second supernatant to obtain a third sediment and a third supernatant, resuspending the third sediment in a cryoprotectant to obtain a mixture, and freeze-drying the mixture to obtain a powdered composition, wherein the powdered composition is substantially tasteless, odorless, and colorless.

Certain further aspects of the example process are described following, any one or more of which may be present in certain embodiments. The example process further includes wherein separating to obtain the first sediment and the first supernatant is accomplished via centrifugation at a high speed. The example process further includes wherein the high speed is greater than 1000×g. The example process further includes wherein the high speed is 8000×g. The example process further includes wherein separating to obtain the second sediment and the second supernatant is accomplished via centrifugation at a low speed. The example process further includes wherein the low speed is 1000×g. The example process further includes wherein separating to obtain the third sediment and the third supernatant is accomplished via centrifugation at a high speed. The example process further includes wherein the high speed is greater than 1000×g. The example process further includes wherein the high speed is 8000×g. The example process further includes wherein the cryoprotectant is D-(+)-Trehalose dihydrate. The example process further includes adding a cryoprotectant to the first supernatant to obtain a mixture, and freeze-drying the mixture to obtain a powdered composition. The example process further includes discarding the second sediment. The example process further includes resuspending the second sediment in a cryoprotectant to obtain a mixture, and freeze-drying the mixture to obtain a powdered composition. The example process further includes discarding the third supernatant. The example process further includes adding a cryoprotectant to the third supernatant to obtain a mixture, and freeze-drying the mixture to obtain a powdered composition.

An example process includes filtering a fecal sample with a filter medium to generate a filtrate, separating particulate matter of the filtrate to obtain a first sediment and a first supernatant, repeatedly resuspending the first sediment and separating particulate matter of the resuspended first sediment to obtain a second sediment and a second supernatant, resuspending the second sediment in a cryoprotectant to obtain a mixture, and freeze-drying the mixture to obtain a powdered composition.

An example tasteless, odorless, and colorless powder is a product of a process including the steps of: filtering a fecal sample with a filter medium to generate a filtrate, separating particulate matter of the filtrate to obtain a first sediment and a first supernatant, resuspending the first sediment in fresh solvent and separating particulate matter of the resuspended first sediment to obtain a second sediment and a second supernatant, diluting the second supernatant with fresh solvent and separating particulate matter out of the second supernatant to obtain a third sediment and a third supernatant, resuspending the third sediment in a cryoprotectant to obtain a mixture which is freeze-dried to obtain a powdered composition.

Certain further aspects of the example powder are described following, any one or more of which may be present in certain embodiments. The example powder further includes adding at least one of a pharmaceutically-acceptable excipient, a filler, a disintegrant, a pharmaceutically-acceptable carrier, a binder, or a lubricant to the mixture. The example powder further includes discarding the second sediment. The example powder further includes resuspending the second sediment in a cryoprotectant to obtain a mixture, and freeze-drying the mixture to obtain a powdered composition. The example powder further includes discarding the third supernatant. The example powder further includes adding a cryoprotectant to at least one of the first supernatant, the second supernatant, or the third supernatant to obtain a mixture, and freeze-drying the mixture to obtain a powdered composition. The example powder further includes filtering a fecal sample with a filter medium to generate a filtrate, separating particulate matter of the filtrate to obtain a first sediment and a first supernatant, adding a cryoprotectant to the first supernatant to obtain a mixture, and freeze-drying the mixture to obtain a powdered composition. The example powder further includes wherein separating to obtain the first sediment and the first supernatant is accomplished via centrifugation at a high speed. The example powder further includes wherein the high speed is greater than 1000×g. The example powder further includes wherein the high speed is 8000×g. The example powder further includes wherein the cryoprotectant is D-(+)-Trehalose dihydrate. In some embodiments, the cryoprotectant is at least one of amino acids (e.g., alanine, glycine, proline), simple sugars (e.g., D-(+)-Trehalose dihydrate, sucrose, glucose, lactose, ribose), dimethyl sulfoxide (DMSO), or glycerol. The example powder further includes subjecting the fecal sample to a high pressure and a high temperature sterilization.

An example tasteless, odorless, and colorless powder is a product of a process including the steps of: filtering a fecal sample with a filter medium to generate a filtrate, separating particulate matter of the filtrate to obtain a first sediment and a first supernatant, adding a cryoprotectant to the first supernatant to obtain a mixture, and freeze-drying the mixture to obtain a powdered composition. The example powder further includes adding at least one of a pharmaceutically-acceptable excipient, a filler, a disintegrant, a pharmaceutically-acceptable carrier, a binder, or a lubricant to the mixture.

An example procedure including operations for treating an autism spectrum disorder (ASD) or a gastrointestinal symptom associated with ASD in a subject in need thereof includes administering to the subject a powdered pharmaceutical composition including a community of fecal bacteria from a stool of a human donor, the powdered pharmaceutical composition created by a process of: filtering a fecal sample with a filter medium to generate a filtrate, separating particulate matter of the filtrate to obtain a first sediment and a first supernatant, repeatedly resuspending the first sediment and separating particulate matter of the resuspended first sediment to obtain a second sediment and a second supernatant, diluting the second supernatant and repeatedly separating particulate matter out of the second supernatant to obtain a third sediment and a third supernatant, resuspending the third sediment in a cryoprotectant to obtain a mixture, and freeze-drying the mixture to obtain the powdered pharmaceutical composition, wherein the powdered pharmaceutical composition is substantially tasteless, odorless, and colorless.

Certain further aspects of the example procedure are described following, any one or more of which may be present in certain embodiments. The example procedure further includes operations for administering a maintenance dose of the powdered pharmaceutical composition. The example procedure further includes operations for administering a maintenance dose of a second powdered pharmaceutical composition including a community of fecal bacteria from a stool of a human donor, the second powdered pharmaceutical composition created by a process of: adding a cryoprotectant to the first supernatant to obtain a second mixture, and freeze-drying the second mixture to obtain a second freeze-dried composition that is powdered. The example procedure further includes wherein administering is divided between administering a loading dose and administering a maintenance dose. The example procedure further includes wherein the loading dose is: a bolus dose on day one, and the bolus dose on day two. The example procedure further includes wherein the maintenance dose is a fraction of the loading dose and is administered daily for a pre-defined number of weeks. The example procedure further includes wherein the pre-defined number of weeks is 16. The example procedure may further include administering a dose over a treatment period which can range from between 1 day and 4 weeks, between 1 month and 6 months, between 6 months and a year, including at least 1 month, at least 2 months, at least 3 months, at least 4 months, at least 5 months, or at least 6 months. The example procedure may further include administering a dose intermittently, such as every 1 month, every 4 months, every 6 months, yearly, or the like. The example procedure further includes wherein the loading dose is delivered via an enema. The example procedure further includes wherein the human donor is the subject. The example procedure further includes operations for discarding the second sediment. The example procedure further includes operations for resuspending the second sediment in a cryoprotectant to obtain a mixture, and freeze-drying the mixture to obtain a powdered composition. The example procedure further includes operations for discarding the third supernatant. The example procedure further includes operations for adding a cryoprotectant to at least one of the first supernatant, the second supernatant, or the third supernatant to obtain a mixture, and freeze-drying the mixture to obtain a powdered composition.

An example procedure including operations for treating an autism spectrum disorder (ASD) or a gastrointestinal symptom associated with ASD in a subject in need thereof includes administering to the subject a powdered pharmaceutical composition including a community of fecal bacteria from a stool of a human donor, the powdered pharmaceutical composition created by a process of: filtering a fecal sample with a filter medium to generate a filtrate, separating particulate matter of the filtrate to obtain a first sediment and a first supernatant, adding a cryoprotectant to the first supernatant to obtain a mixture, and freeze-drying the mixture to obtain a powdered composition.

Certain further aspects of the example procedure are described following, any one or more of which may be present in certain embodiments. The example procedure further includes wherein administering is divided between administering a loading dose and administering a maintenance dose. The example procedure further includes wherein the loading dose is: a bolus dose on day one, and the bolus dose on day two. The example procedure further includes wherein the maintenance dose is a fraction of the loading dose and is administered daily for a pre-defined number of weeks. The example procedure further includes wherein the pre-defined number of weeks is 16. The example procedure further includes wherein the loading dose is delivered via an enema. The example procedure further includes wherein the human donor is the subject.

An example procedure including operations for treatment of a subject with colitis, Crohn's, Parkinson's disease, Alzheimer's disease, metabolic disorders, autism spectrum disorder, multiple sclerosis, neuropsychiatric conditions, post-cancer, chronic digestive issues, gastrointestinal issues, inflammatory bowel disease (IBD), irritable bowel syndrome (IBS), anti-aging or any condition being studied or approved for treatment via microbial transfer includes administering to the subject a powdered pharmaceutical composition including a community of fecal bacteria from a stool of a human donor, the powdered pharmaceutical composition created by a process of: filtering a fecal sample with a filter medium to generate a filtrate, separating particulate matter of the filtrate to obtain a first sediment and a first supernatant, repeatedly resuspending the first sediment and separating particulate matter of the resuspended first sediment to obtain a second sediment and a second supernatant, diluting the second supernatant and repeatedly separating particulate matter out of the second supernatant to obtain a third sediment and a third supernatant, resuspending the third sediment in a cryoprotectant to obtain a mixture, and freeze-drying the mixture to obtain a the powdered pharmaceutical composition, wherein the powdered pharmaceutical composition is substantially tasteless, odorless, and colorless.

Certain further aspects of the example procedure are described following, any one or more of which may be present in certain embodiments. The example procedure further includes administering a maintenance dose of a second powdered pharmaceutical composition including a community of fecal bacteria from a stool of a human donor, the second powdered pharmaceutical composition created by a process of: adding a cryoprotectant to the first supernatant to obtain a second mixture, and freeze-drying the second mixture to obtain a second freeze-dried composition, wherein the second freeze-dried composition is powdered. The example procedure further includes wherein administering is divided between administering a loading dose and administering a maintenance dose. The example procedure further includes wherein the loading dose is: a bolus dose on day one, and the bolus dose on day two. The example procedure further includes wherein the maintenance dose is a fraction of the loading dose and is administered daily for a pre-defined number of weeks. The example procedure further includes wherein the pre-defined number of weeks is 16. The example procedure further includes wherein the loading dose is delivered via an enema. The example procedure further includes wherein the human donor is the subject. The example procedure further includes discarding the second sediment. The example procedure further includes resuspending the second sediment in a cryoprotectant to obtain a mixture, and freeze-drying the mixture to obtain a powdered composition. The example procedure further includes discarding the third supernatant. The example procedure further includes adding a cryoprotectant to at least one of the first supernatant, the second supernatant, or the third supernatant to obtain a mixture, and freeze-drying the mixture to obtain a powdered composition.

An example procedure including operations for treatment of a subject with colitis, Crohn's, Parkinson's, Alzheimer's, post-cancer, chronic digestive issues, gastrointestinal issues, or any condition being studied or approved for treatment via microbial transfer includes administering to the subject a powdered pharmaceutical composition including a community of fecal bacteria from a stool of a human donor, the powdered pharmaceutical composition created by a process of: filtering a fecal sample with a filter medium to generate a filtrate, separating particulate matter of the filtrate to obtain a first sediment and a first supernatant, adding a cryoprotectant to the first supernatant to obtain a mixture, and freeze-drying the mixture to obtain the powdered pharmaceutical composition.

Certain further aspects of the example procedure are described following, any one or more of which may be present in certain embodiments. The example procedure further includes wherein administering is divided between administering a loading dose and administering a maintenance dose. The example procedure further includes wherein the loading dose is: a bolus dose on day one, and the bolus dose on day two. The example procedure further includes wherein the maintenance dose is a fraction of the loading dose and is administered daily for a pre-defined number of weeks. The example procedure further includes wherein the pre-defined number of weeks is 16. The example procedure further includes wherein the loading dose is delivered via an enema. The example procedure further includes wherein the human donor is the subject.

An example procedure including operations for treating an autism spectrum disorder (ASD) in a subject in need thereof includes administering to the subject an amount of a pharmaceutical composition effective for treating said ASD, wherein the pharmaceutical composition includes a fecal microbe preparation prepared via a process including: filtering a fecal sample with a filter medium to generate a filtrate, separating particulate matter of the filtrate to obtain a first sediment and a first supernatant, repeatedly resuspending the first sediment and separating particulate matter of the resuspended first sediment to obtain a second sediment and a second supernatant, diluting the second supernatant and repeatedly separating particulate matter out of the second supernatant to obtain a third sediment and a third supernatant, resuspending the third sediment in a cryoprotectant to obtain a mixture, and freeze-drying the mixture to obtain a powdered composition, wherein the powdered composition is substantially tasteless, odorless, and colorless, wherein the subject exhibits at least a 10% reduction in ASD symptom severity after the administering as compared to before the administering, and based on an assessment system selected from a group consisting of Childhood Autism Rating Scale (CARS), Childhood Autism Rating Scale 2—Standard Form (CARS2-ST), and Childhood Autism Rating Scale 2—High Functioning (CARS2-HF).

Certain further aspects of the example procedure are described following, any one or more of which may be present in certain embodiments. The example procedure further includes administering a maintenance dose of a second pharmaceutical composition including a community of fecal bacteria from a stool of a human donor, the second pharmaceutical composition created by the process of: adding a cryoprotectant to the first supernatant to obtain a second mixture, and freeze-drying the second mixture to obtain a second freeze-dried, powdered composition. The example procedure further includes wherein administering is divided between administering a loading dose and administering a maintenance dose. The example procedure further includes wherein the loading dose is: a bolus dose on day one, and the bolus dose on day two. The example procedure further includes wherein the maintenance dose is a fraction of the loading dose and is administered daily for a pre-defined number of weeks. The example procedure further includes wherein the pre-defined number of weeks is 16. The example procedure further includes wherein the loading dose is delivered via an enema. The example procedure further includes wherein the fecal sample is from the subject. The example procedure further includes discarding the second sediment. The example procedure further includes resuspending the second sediment in a cryoprotectant to obtain a mixture, and freeze-drying the mixture to obtain a powdered composition. The example procedure further includes discarding the third supernatant. The example procedure further includes adding a cryoprotectant to at least one of the first supernatant, the second supernatant, or the third supernatant to obtain a mixture, and freeze-drying the mixture to obtain a powdered composition.

An example procedure including operations for treating an autism spectrum disorder (ASD) in a subject in need thereof includes administering to the subject an amount of a pharmaceutical composition effective for treating said ASD, wherein the pharmaceutical composition includes a fecal microbe preparation prepared via a process including: filtering a fecal sample with a filter medium to generate a filtrate, separating particulate matter of the filtrate to obtain a first sediment and a first supernatant, adding a cryoprotectant to the first supernatant to obtain a mixture, and freeze-drying the mixture to obtain a powdered composition, wherein the subject exhibits at least a 10% reduction in ASD symptom severity after the administering as compared to before the administering, and based on an assessment system selected from a group consisting of Childhood Autism Rating Scale (CARS), Childhood Autism Rating Scale 2—Standard Form (CARS2-ST), and Childhood Autism Rating Scale 2—High Functioning (CARS2-HF).

Certain further aspects of the example procedure are described following, any one or more of which may be present in certain embodiments. The example procedure further includes wherein administering is divided between administering a loading dose and administering a maintenance dose. The example procedure further includes wherein the loading dose is: a bolus dose on day one, and the bolus dose on day two. The example procedure further includes wherein the maintenance dose is a fraction of the loading dose and is administered daily for a pre-defined number of weeks. The example procedure further includes wherein the pre-defined number of weeks is 16. The example procedure further includes wherein the loading dose is delivered via an enema. The example procedure further includes wherein the fecal sample is from the subject.

In some aspects, the techniques described herein relate to a method of dividing human fecal matter into useful output products, including at least one fecal microbiota transplant (FMT) having palatable odor and flavor, the method including: a) suspending and filtering a fecal sample acquired from a fecal donor, thereby generating a filtrate including desired fecal microbes of the fecal sample and a residue; b) centrifuging the filtrate at a first gravitational force of between 6000×g and 10,000×g, including 8000×g, for a first centrifugation length of time of between 2 min and 60 min, including 20 min, and optionally resuspending and repeating the centrifuging once, twice, or more, thereby resulting in a first supernatant and a first pellet, the first pellet including the desired fecal microbes; c) resuspending the first pellet and centrifuging at between 250×g and 2000×g, including 1000×g, for between 2 min and 60 min, including 20 min, and optionally decanting the supernatant and repeating the centrifuging once, twice, or more, thereby resulting in a second supernatant and a second pellet, the second supernatant including the desired fecal microbes; d) centrifuging the second supernatant or a dilution of the second supernatant at between 6000×g and 10,000×g, including 8000×g, for between 2 min and 60 min, including 20 min, and optionally resuspending and repeating the centrifuging once, twice, or more, thereby resulting in a third supernatant and a third pellet, the third pellet including the desired fecal microbes; e) resuspending the third pellet in the presence of a cryoprotectant, thereby producing a refined suspension including the desired fecal microbes; f) freezing the refined suspension; g) freeze-drying the frozen refined suspension, thereby providing the FMT; and h) down-stream processing the residue, the first supernatant, the second pellet, and/or the third supernatant, thereby producing a downstream product.

In some aspects, the techniques described herein relate to a method of preparing a fecal microbiota transplant (FMT) having palatable odor and flavor to facilitate non-encapsulated oral administration in large doses, the method including the following steps: a) suspending and filtering a fecal sample acquired from a fecal donor, thereby generating a filtrate including desired fecal microbes of the fecal sample;

b) centrifuging the filtrate at a first gravitational force of between 6000×g and 10,000×g, including 8000×g, for a first centrifugation length of time of between 2 min and 60 min, including 20 min, and optionally resuspending and repeating the centrifuging once, twice, or more, thereby resulting in a first supernatant and a first pellet, the first pellet including the desired fecal microbes; c) resuspending the first pellet and centrifuging at between 250×g and 2000×g, including 1000×g, for between 2 min and 60 min, including 20 min, and optionally decanting the supernatant and repeating the centrifuging once, twice, or more, thereby resulting in a second supernatant and a second pellet, the second supernatant including the desired fecal microbes; d) centrifuging the second supernatant or a dilution of the second supernatant at between 6000×g and 10,000×g, including 8000×g, for between 2 min and 60 min, including 20 min, and optionally resuspending and repeating the centrifuging once, twice, or more, thereby resulting in a third supernatant and a third pellet, the third pellet including the desired fecal microbes; e) resuspending the third pellet in the presence of a cryoprotectant, thereby producing a refined suspension including the desired fecal microbes; f) freezing the refined suspension; and g) freeze-drying the frozen refined suspension, thereby providing the FMT.

In some aspects, the techniques described herein relate to a the method of any one of the six immediately preceding claims, wherein the triangular test is ISO 4120.

In some aspects, the techniques described herein relate to a method of orally administering a fecal microbiota transplant (FMT) composition with improved compliance to a subject, the method including: orally administering 50 billion CFUs of the FMT composition to the subject in 2 days or less.

In some aspects, the techniques described herein relate to a method of orally administering a fecal microbiota transplant (FMT) composition to a subject without requiring swallowing whole of an encapsulated dosage form, the method including: orally administering 50 billion CFUs of the FMT composition to the subject, wherein the composition is in direct contact with the subject's tongue during the orally administering.

In some aspects, the techniques described herein relate to a method of treating a subject having been diagnosed with autism spectrum disorder (ASD), the method including: administering a predetermined loading dose for a fecal microbiota transplant (FMT) composition under a loading dose protocol; and administering a predetermined maintenance dose of the FMT under a maintenance dose protocol, wherein either the loading dose protocol or the maintenance dose protocol requires orally administering 50 billion CFUs.

In some aspects, the techniques described herein relate to a method of dividing human fecal matter into useful output products, including at least one fecal microbiota transplant (FMT) having palatable odor and flavor, the method including: (a) suspending a fecal sample acquired from a fecal donor in a first volume; (b) filtering the suspended fecal sample thereby generating a first filtrate including desired fecal microbes of the fecal sample and a residue; (c) filtering the suspended fecal sample a second time thereby generating a second filtrate and additional residue; (d) adding a second volume of fresh solvent to the suspended fecal sample; (e) filtering the suspended fecal sample thereby generating a third filtrate and additional residue; (f) filtering the suspended fecal sample thereby generating a fourth filtrate and additional residue; (g) filtering the suspended fecal sample thereby generating a fifth filtrate and additional residue; (h) filtering the suspended fecal sample thereby generating a sixth filtrate and additional residue; (i) centrifuging, in separate containers, the first filtrate, the second filtrate, the third filtrate, the fourth filtrate, the fifth filtrate, and the sixth filtrate at a first gravitational force of between 6000×g and 10,000×g, including 8000×g, for a first centrifugation length of time of between 2 min and 60 min, including 20 min and discarding a first supernatant from each of the separate containers; (j) adding a third volume of fresh solvent to each container, resuspending a first sediment in each container, and centrifuging each container at the first gravitational force of between 6000×g and 10,000×g, including 8000×g, for the first centrifugation length of time of between 2 min and 60 min, including 20 min and discarding a second supernatant from each of the separate containers; (k) adding a fourth volume of fresh solvent to each container, resuspending a second sediment in each container, and centrifuging each container at the first gravitational force of between 6000×g and 10,000×g, including 8000×g, for the first centrifugation length of time of between 2 min and 60 min, including 20 min and discarding a third supernatant from each of the separate containers; (l) adding a fifth volume of fresh solvent to each container, resuspending a third sediment in each container, centrifuging at a second gravitational force between 250×g and 2000×g, including 1000×g, for between 2 min and 60 min, including 20 min, decanting a fourth supernatant from each container to a new container, and diluting the fourth supernatant in each new container with fresh solvent to reach a predetermined volume; (m) centrifuging each new container at the second gravitational force between 250×g and 2000×g, including 1000×g, for between 2 min and 60 min, including 20 min, decanting a fifth supernatant from each new container to a second new container, and diluting the fifth supernatant in each second new container with fresh solvent to reach the predetermined volume; (n) centrifuging each second new container at the second gravitational force between 250×g and 2000×g, including 1000×g, for between 2 min and 60 min, including 20 min, and decanting a sixth supernatant from each second new container to a third new container; (o) diluting the sixth supernatant in each third new container with fresh solvent to reach the predetermined volume, centrifuging each third new container at a third gravitational force of between 6000×g and 10,000×g, including 8000×g, for a third centrifugation length of time of between 2 min and 60 min, including 20 min, discarding a seventh supernatant from each of the third new containers, and obtaining a fourth sediment; (p) resuspending the fourth sediment in each third new container in the presence of a cryoprotectant, thereby producing a refined suspension in each third new container including desired fecal microbes; f) freezing the refined suspension; and g) freeze-drying the frozen refined suspension, thereby providing the FMT.

In some aspects, the techniques described herein relate to a method of preparing a fecal microbiota transplant (FMT) having palatable odor and flavor to facilitate non-encapsulated oral administration in large doses, the method including the following steps: a) suspending and filtering a fecal sample acquired from a fecal donor, thereby generating a filtrate including desired fecal microbes of the fecal sample and a residue; b) centrifuging the filtrate at a first gravitational force of between 6000×g and 10,000×g for a first centrifugation length of time of between 2 min and 60 min and optionally resuspending and repeating the centrifuging once, twice, or more, thereby resulting in a first supernatant and a first pellet, the first pellet including the desired fecal microbes; c) resuspending the first pellet and centrifuging at a second gravitational force of between 250×g and 2000×g for a second centrifugation length of time of between 2 min and 60 min and optionally decanting the supernatant and repeating the centrifuging once, twice, or more, thereby resulting in a second supernatant and a second pellet, the second supernatant including the desired fecal microbes; d) centrifuging the second supernatant or a dilution of the second supernatant at a third gravitational force of between 6000×g and 10,000×g for a third centrifugation length of time of between 2 min and 60 min and optionally resuspending and repeating the centrifuging once, twice, or more, thereby resulting in a third supernatant and a third pellet, the third pellet including the desired fecal microbes; e) resuspending the third pellet in the presence of a cryoprotectant, thereby producing a refined suspension including the desired fecal microbes; f) freezing the refined suspension; and g) freeze-drying the frozen refined suspension, thereby providing the FMT.

In some aspects, the techniques described herein relate to a process including: filtering a fecal sample with a filter medium to generate a filtrate; separating particulate matter of the filtrate to obtain a first sediment and a first supernatant; repeatedly resuspending the first sediment and separating particulate matter of the resuspended first sediment to obtain a second sediment and a second supernatant; diluting the second supernatant and repeatedly separating particulate matter out of the second supernatant to obtain a third sediment and a third supernatant; resuspending the third sediment in a cryoprotectant to obtain a mixture; and freeze-drying the mixture to obtain a powdered composition, wherein the powdered composition is substantially tasteless and odorless.

In some aspects, the techniques described herein relate to a fecal microbiota transplant (FMT) composition for oral delivery, the FMT composition including an FMT including desired fecal microbes, wherein the FMT has an odor as evaluated with a confidence of 95% to be odorless for more than 50% of the population using a triangular test, wherein the FMT has a flavor as evaluated with a confidence of 80% to be flavorless for more than 50% of the population using the triangular test.

In some aspects, the techniques described herein relate to an FMT made by a method, the method including: a) suspending and filtering a fecal sample acquired from a fecal donor, thereby generating a filtrate including desired fecal microbes of the fecal sample and a residue; b) centrifuging the filtrate at a first gravitational force of between 6000×g and 10,000×g for a first centrifugation length of time of between 2 min and 60 min and optionally resuspending and repeating the centrifuging once, twice, or more, thereby resulting in a first supernatant and a first pellet, the first pellet including the desired fecal microbes; c) resuspending the first pellet and centrifuging at a second gravitational force of between 250×g and 2000×g for a second centrifugation length of time of between 2 min and 60 min and optionally decanting the supernatant and repeating the centrifuging once, twice, or more, thereby resulting in a second supernatant and a second pellet, the second supernatant including the desired fecal microbes; d) centrifuging the second supernatant or a dilution of the second supernatant at a third gravitational force of between 6000×g and 10,000×g for a third centrifugation length of time of between 2 min and 60 min and optionally resuspending and repeating the centrifuging once, twice, or more, thereby resulting in a third supernatant and a third pellet, the third pellet including the desired fecal microbes; e) resuspending the third pellet in the presence of a cryoprotectant, thereby producing a refined suspension including the desired fecal microbes; f) freezing the refined suspension; and g) freeze-drying the frozen refined suspension, thereby providing the FMT.

In some aspects, the techniques described herein relate to a tasteless and odorless powder, wherein the powder is a product of a process including the steps of: filtering a fecal sample with a filter medium to generate a filtrate; separating particulate matter of the filtrate to obtain a first sediment and a first supernatant; repeatedly resuspending the first sediment and separating particulate matter of the resuspended first sediment to obtain a second sediment and a second supernatant; diluting the second supernatant and repeatedly separating particulate matter out of the second supernatant to obtain a third sediment and a third supernatant; resuspending the third sediment in a cryoprotectant to obtain a mixture; and freeze-drying the mixture to obtain a powdered composition.

In some aspects, the techniques described herein relate to a method of orally administering a fecal microbiota transplant (FMT) composition with improved compliance to a subject, the method including: orally administering the FMT composition to the subject, wherein the FMT composition includes an FMT including desired fecal microbes, wherein the FMT has an odor as evaluated with a confidence of 95% to be odorless for more than 50% of the population using a triangular test, wherein the FMT has a flavor as evaluated with a confidence of 80% to be flavorless for more than 50% of the population using the triangular test.

In some aspects, the techniques described herein relate to a method of orally administering a fecal microbiota transplant (FMT) composition with improved compliance to a subject, the method including: orally administering 50 billion CFUs of the FMT composition to the subject in 2 days or less.

In some aspects, the techniques described herein relate to a method of orally administering a fecal microbiota transplant (FMT) composition to a subject without requiring swallowing whole of an encapsulated dosage form, the method including: orally administering 50 billion CFUs of the FMT composition to the subject, wherein the composition is in direct contact with the subject's tongue during the orally administering.

These and other systems, methods, objects, features, and advantages of the present disclosure will be apparent to those skilled in the art from the following detailed description of the preferred embodiment and the drawings.

All documents mentioned herein are hereby incorporated in their entirety by reference. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context.

BRIEF DESCRIPTION OF THE FIGURES

The disclosure and the following detailed description of certain embodiments thereof may be understood by reference to the following figures:

FIG. 7 depicts a procedure for treating autism spectrum disorder.

FIG. 8 depicts a system for production of FMT.

FIG. 9 is a flowchart of an example method for dividing human fecal matter into useful output products.

DETAILED DESCRIPTION

Figure 1:
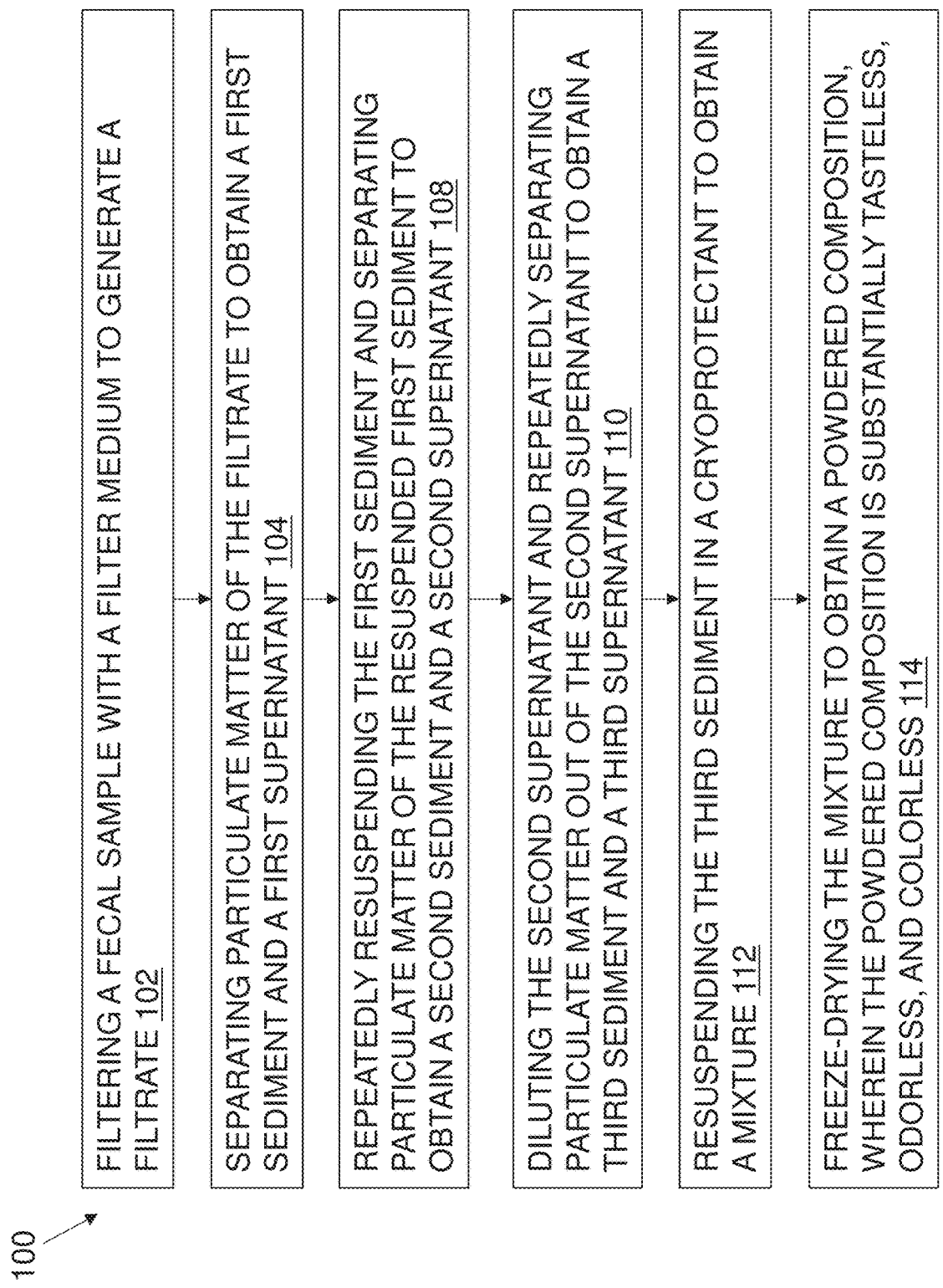
FIG. 1 depicts a procedure for preparing an FMT composition.

In an aspect, the disclosure herein provides compositions for FMT that may include fecal microbes. The term FMT is used throughout this specification, but it is understood that the following terms may also be used and are interchangeable: FMT is used here, but it is understood that the following terms or phrases are interchangeable: stool transplantation or transfer, microbial reconstitution therapy (MRT), intestinal microbiota transplant (IMT), or microbiota transfer therapy (MTT).

As used herein, the term "fecal microbes" refers to microorganisms that are present in the mammalian gastrointestinal system, including any of the gut, intestine, colon, and the like. Compositions may be prepared by processing fecal samples derived from mammalian stool, as described herein. Fecal samples may comprise microbial/biological material as well as non-living material, such as waste products, undigested food materials, dead bacteria, shed host cells, proteins, carbohydrates, fats, minerals, mucus, bile, and the like.

As used herein, the term "desired fecal microbes" refers to a specific subset of the fecal microbes that are selected based on possession of one or more desirable properties. In some cases, the desirable properties include desirable therapeutic properties that come from administration of the desired fecal microbes. In some cases, the desirable properties include excellent survivability. In some cases, the desired fecal microbes include microbes of one species, two species, three species, four species, five species, or six, seven, eight, nine, or ten or more species of microbe. In some cases, the desired fecal microbes are the full microbiome of an individual or group of individuals, whether selected based on overall desirability of the microbiome or based on a particular desirability of the microbiome for a specific purpose.

As used herein, the term "orally deliverable powder" refers to an odorless and tasteless powder form of a composition for FMT that is designed to be administered orally or suspended in any liquid and does not require encapsulation for oral delivery. In some aspects, an orally deliverable powder is a pharmaceutical powder which is intended to be orally administered and is formulated to provide a therapeutically active substance when consumed. In some aspects, an orally deliverable powder is a pharmaceutical product, without odor or taste, which is delivered orally without need for encapsulation, in a powdered form or suspended in any liquid. In some aspects, orally deliverable powders are aesthetically acceptable due to reduced odor, which may be a result of a decreased presence of volatile organic molecules relative to powders that are not orally deliverable. Powders that are not orally deliverable may include: any powdered FMT product that is not palatable due to odor, increased presence of volatile organic molecules, taste, or unappealing colors; compositions for FMT that, without encapsulation, could cause harm when ingested; or a composition for FMT that without encapsulation would cause the beneficial microbe to break down before entering the GI tract and/or a location within the gut microbiome that would allow for engraftment of the fecal microbes.

In an embodiment, and referring to FIG. 1, an example procedure 100 may include an operation 102 of filtering a fecal sample with a filter medium to generate a filtrate, an operation 104 of separating particulate matter of the filtrate to obtain a first sediment and a first supernatant, an operation 108 of repeatedly resuspending the first sediment in fresh solvent and separating particulate matter of the resuspended first sediment to obtain a second sediment and a second supernatant, an operation 110 of diluting the second supernatant with fresh solvent and repeatedly separating particulate matter out of the second supernatant to obtain a third sediment and a third supernatant, an operation 112 of resuspending the third sediment in a cryoprotectant to obtain a mixture, and an operation 114 of freeze-drying the mixture to obtain a powdered composition, wherein the powdered composition may be substantially tasteless, odorless, and colorless. In embodiments, fecal samples may be taken from a donor who is not the subject, or fecal samples may be autologous, that is, taken from the donor themselves, for example, such as from fecal matter banked prior to a time for the need for FMT. In certain embodiments, fecal samples may be processed within a time period from collection, such as within 24 hours. Certain criteria for the fecal sample may be applied, such as certain desired pH's or pH ranges, and only certain types of stool as described on the Bristol stool chart may be processed (e.g., Type 2, Type 3, or Type 4). An initial visual observation for blood or mucus may also be used to exclude certain fecal samples from further processing.

A quantity of the fecal sample may be diluted with saline or other desired solvent in preparation for filtration. For example, 100 gm of a stool sample may be diluted with 400 ml of saline or other appropriate diluent to obtain a slurry. The slurry may be filtered using any available filtration technique, such as a bag filter with a perforated or microperforated filter, membrane filters, paper filters, and the like. In an example, the stool sample may be placed into the bag filter and the diluent added to the bag with the bag being placed into a bag mixer for further processing. The bag may be acted upon by the bag mixer for a duration of time such as 1 minute, 2 minutes, 5 minutes, 10 minutes, and the like. Processing results in a filtered solution (also known as a filtrate) which may be drawn out of the bag and placed into another vessel for further processing. The process may be repeated for the same duration of time, or for shorter or longer times, to obtain additional filtered solution. Additional diluent, such as an additional 100 ml, may be added to the bag and the process may be repeated for the same duration of time, or for shorter or longer times, to obtain additional filtered solution. In embodiments, the filtered solution obtained in any of the processing or further processing steps may be combined for subsequent processing steps. It should be understood that at any of the steps of dilution and/or resuspension, the amount of diluent utilized may be limited to improve the concentration of microbes in the sample or to optimize further processing steps, such as freeze-drying. It should be understood that the diluent or any other reagent used in the methods may be sterile or not.

In embodiments, the filtrate may be subjected to separation to separate particulate matter from the filtrate and obtain a first sediment (also known as settled material or a pellet) and a first supernatant. For example, separating to obtain the first sediment and the first supernatant may be accomplished via centrifugation. In an example, centrifugation may proceed at high speed, such as at a speed providing a relative centrifugal force (RCF) that is greater than 1000×g. In some embodiments, the speed is 8000×g. In other examples, as will be described herein, centrifugation may proceed at lower speeds, such as speeds below 1000×g. Without adhering to any particular thesis, it may be understood that microbes are concentrated in the sediment when separated at high speed, while the metabolome, or metabolic products/metabolites, may be concentrated in the supernatant at low speeds.

In embodiments, after the initial separation that results in the first sediment and the first supernatant, both materials may be available for further processing. For example, a cryoprotectant may be added to the first supernatant to obtain a mixture, and the mixture may be freeze-dried, such as by using a freeze dryer, to obtain a freeze-dried, powdered composition. Examples of cryoprotectants may include, but are not limited to amino acids (e.g., alanine, glycine, proline), simple sugars (e.g., D-(+)-Trehalose dihydrate, sucrose, glucose, lactose, ribose), dimethyl sulfoxide (DMSO), glycerol, or the like. The amount of cryoprotectant present in a composition described herein may vary depending on the cryoprotectant used and the temperature to be used for freezing (e.g., one cryoprotectant used at −20 C may not be preferred for use at −80 C). For example, the cryoprotectant may be 5% D-(+)Trehalose dihydrate. In an example, 32 ml of cryoprotectant may be used to resuspend or dilute the material being freeze-dried. Prior to freeze-drying, the mixture may be subjected to a dwell time at low temperature, such as at −80 deg. Celsius for times ranging from 1 to 24 hours or more. In embodiments, freeze-drying may occur over the course of many hours to many days. Throughout this Specification, it should be understood that freeze-drying may be preceded by freezing.

In embodiments, the first sediment may be further processed by resuspending it in a fresh diluent, such as saline. For example, to the centrifuge tube containing the pellet, fresh saline may be added and the material may be resuspended, such as by agitation, shaking, vibrating with a vortex machine, or the like. For example, 45 ml of saline or other appropriate diluent may be added to the tube. Subsequent to the resuspension, the material in the tube may again be subjected to separation, such as centrifugation at high speed, such as greater than 1000×g, and at 8000×g in some embodiments. The duration of separation may be in a range of 1 min to 25 min, 2 min to 30 min, or 30 sec to 25 min. For example, the duration may be 20 min. Separation may proceed at low temperature, such as at 4 deg. Celsius or other suitable temperature that preserves the biological materials being processed. Each round of resuspension of the first sediment and centrifugation may be known as a wash. After each wash, the supernatant may either be discarded or subjected to freeze-drying in the presence of a cryoprotectant (such as 32 ml of 5% D-(+)Trehalose dihydrate), as described herein. In embodiments, any number of wash cycles may be employed. For example, once the first sediment is resuspended after the first time it is centrifuged, no further wash cycles may be employed and the process may continue with steps aimed at obtaining the second sediment and second supernatant. In other examples, two, three, or more wash cycles may be employed. Each wash cycle may proceed at high speed, such as at 8000×g. After the final wash cycle, the washed first sediment is resuspended, such as in a quantity of fresh saline (e.g., 45 ml), in preparation for the next step of processing.

Figure 2:
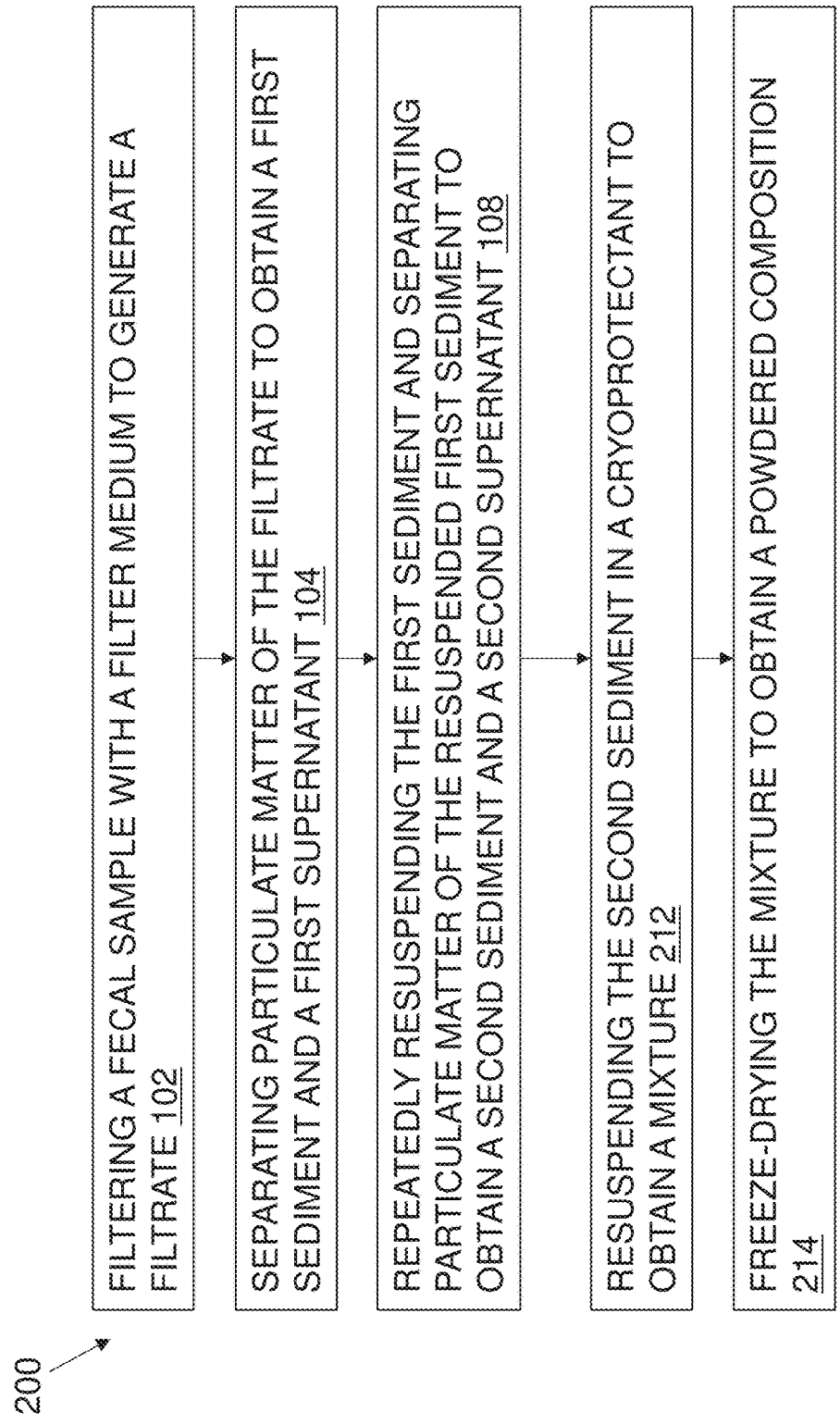
FIG. 2 depicts a procedure for preparing an FMT composition.

In embodiments, the resuspended first sediment is subject to further separation, however, lower speeds may be used in this step to obtain a second sediment and a second supernatant. The duration of separation may be in a range of 1 min to 25 min, 2 min to 30 min, or 30 sec to 25 min. For example, the resuspended first sediment may be centrifuged at 1000×g for 20 minutes at 4 deg. Celsius to obtain a second sediment and a second supernatant. The second supernatant is transferred into a new tube while the second sediment is resuspended in a fresh diluent, such as 45 ml saline, and subjected to centrifugation at low speed, such as for a duration of 20 minutes and at a low temperature. Once again, the supernatant is drawn off, the pellet is resuspended (e.g., in a fresh solvent/diluent), and the resuspended second sediment is once again centrifuged. Each of the resuspension/centrifugation cycles is known as a wash cycle. After a number of wash cycles, such as between 1 and 3 or 4 wash cycles, a quantity of supernatant, the washed second supernatant, that was drawn off after each cycle is available for further processing. In certain embodiments, the further processing may be to freeze-dry the washed second supernatant in the presence of a cryoprotectant, as described herein. In certain embodiments, and referring to FIG. 2, the further processing may be to resuspend the second sediment in a cryoprotectant to obtain a mixture 212, and freeze-dry the mixture to obtain a freeze-dried, powdered composition 214. In other embodiments, the further processing may be separation of the second supernatant to obtain a third sediment and a third supernatant. In some embodiments, the second sediment may be discarded.

In embodiments, the second supernatant may be subjected to further separation. Separating to obtain the third sediment and the third supernatant may be accomplished via centrifugation at a high speed, such as speeds greater than 1000×g, such as 8000×g. The duration of separation may be in a range of 1 min to 25 min, 2 min to 30 min, or 30 sec to 25 min. As described herein, separation may proceed for a duration of time at low temperature, such as for 20 minutes. In embodiments, the third supernatant may be discarded, or a cryoprotectant may be added and the third supernatant and the mixture may be freeze-dried, as described herein. In embodiments, a cryoprotectant may be added to the third sediment and the mixture may be freeze-dried, as described herein, to produce a powdered composition. The powdered composition may be a tasteless, odorless, and colorless powder. The powdered composition may be conveniently administered in a form containing one or more pharmaceutically acceptable carriers, such as diluents or excipients such as fillers, binders, wetting agents, disintegrators, surface-active agents, glidants, lubricants, food products, or the like. For example, given that the powdered composition may be substantially tasteless, odorless, and colorless, it may be sprinkled on food, mixed into a smoothie/shake (e.g., such as smoothies including protein powders), mixed with water, mixed into juice/water/milk, mixed into a spread, or the like, or ingested directly. In some embodiments, the powdered composition may be processed into other orally available formulations, such as by encapsulation, tableting, and the like.

Figure 3:
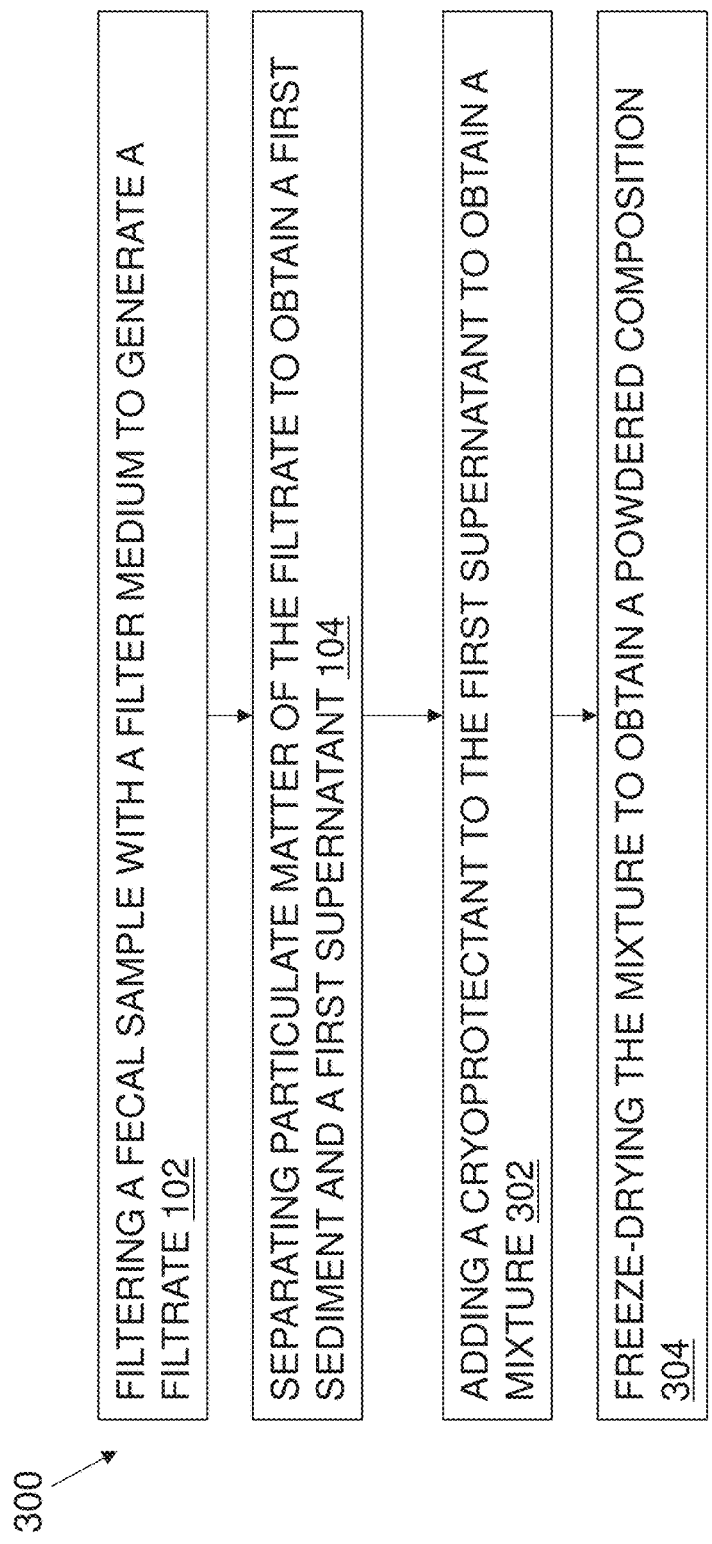
FIG. 3 depicts a procedure for preparing an FMT composition.

It should be understood that any of the first supernatant, the second supernatant, or the third supernatant may be mixed with a cryoprotectant, and freeze-dried as described herein to obtain a composition, such as a powdered composition that may be substantially tasteless, odorless, and colorless. It should also be understood that any of the first sediment, the second sediment, or the third sediment may be resuspended in a cryoprotectant, and freeze-dried as described herein to obtain a composition, such as a powdered composition that may be substantially tasteless, odorless, and colorless. For example, and referring to FIG. 3, a cryoprotectant is added to the first supernatant to obtain a mixture 302, and the mixture is freeze-dried to obtain a freeze-dried, powdered composition 304, wherein the powdered composition may be substantially tasteless, odorless, and colorless.

It should be understood that the fecal sample may also undergo optional pre-processing, such as subjecting the fecal sample to a high pressure and a high temperature sterilization, such as via autoclaving.

In certain aspects, the present disclosure provides a method of preparing a fecal microbiota transplant (FMT). The FMT can be an orally deliverable powder. The FMT can be tasteless. The FMT can be substantially odorless. The FMT can have low coloration. The FMT can have palatable odor and flavor directly in its powder form without required traditional encapsulation or masking. This FMT can facilitate non-encapsulated oral administration in both small and large doses with concentrated beneficial microbes. Doses of FMT may include a quantity of desired fecal microbes delivered orally in a given window of time.

Administering doses of FMT may be over a treatment period which can range from between 1 day and 4 weeks, between 1 month and 6 months, between 6 months and a year, including at least 1 month, at least 2 months, at least 3 months, at least 4 months, at least 5 months, or at least 6 months. Administering doses of FMT may include administering a dose intermittently, such as every 1 month, every 4 months, every 6 months, yearly, or the like. In some cases, the doses are administered consecutively and in other cases, doses may be staggered. In some cases, depending on the condition or health state, a small dose will be administered over a short period including hours or days. In some cases, depending on the condition or health state, a repeated small dose will be administered, after a large dose, over a long period including days, weeks, or years. In some cases, depending on the condition or health state, a repeated small dose will be administered over a long period, including days, weeks, or years. In some cases, depending on the condition or health state, a large dose will be administered over a short period, including hours or days. In some cases, depending on the condition or health state, a repeated large dose will be administered over a long period, including days, weeks, or years.

Prior to this discovery, oral administration of FMT required either strong odor and flavor masking agents (e.g., chocolate milk) or encapsulation. The inventors unexpectedly discovered that carefully processing fecal samples can facilitate the production of a powdered composition containing desired fecal microbes, which is palatable in the absence of masking agents or physical barriers such as capsules and orally deliverable to individuals who are unable or resistant to swallow a capsule. With the understanding that this patent application may be pursued in various jurisdictions, and without wishing to be bound by any particular legal theory of inventiveness, it is believed that patent protection is generally available for the discovery of a process and resulting composition for achieving all of the following: 1) transforming a typically-unpalatable material in human fecal matter into a palatable material; 2) achieving the first goal without killing desired fecal microbes; 3) providing a composition that can be deployed for practical usage without requiring extreme storage conditions (e.g., such as a liquid nitrogen-based or medical grade low temperature freezers); 4) achieving a degree of palatability that allows oral administration without requiring encapsulation (or other physical barrier between composition and tongue); and 5) achieving a degree of palatability that allows non-encapsulated oral delivery without requiring appreciable flavor or odor masking.

The inventors surprisingly discovered that a process using conventional processing steps applied in a way that had not previously been contemplated could overcome the shortcomings of current oral FMT delivery systems. In an aspect, the present disclosure provides a method of preparing a FMT having palatable odor and flavor to facilitate non-encapsulated oral administration in large, or small, doses of concentrated beneficial microbes. In one particular aspect, impressively large doses of microbes can be delivered. The composition for FMT is substantially tasteless and odorless and can be easily ingested as a powder or suspended in a liquid. The method includes: a) suspending and filtering a fecal sample acquired from a fecal donor, thereby generating a filtrate including desired fecal microbes of the fecal sample; b) centrifuging the filtrate at a first gravitational force of between 6000×g and 10,000×g, including 8000×g, for a first centrifugation length of time of between 2 min and 60 min, including 20 min, and optionally resuspending and repeating the centrifuging once, twice, or more, thereby resulting in a first supernatant and a first pellet, the first pellet including the desired fecal microbes; c) resuspending the first pellet and centrifuging at a second gravitational force of between 250×g and 2000×g, including 1000×g, for a second centrifugation length of time of between 2 min and 60 min, including 20 min, and optionally decanting the supernatant and repeating the centrifuging once, twice, or more, thereby resulting in a second supernatant and a second pellet, the second supernatant including the desired fecal microbes; d) centrifuging the second supernatant or a dilution of the second supernatant at a third gravitational force of between 6000×g and 10,000×g, including 8000×g, for a third centrifugation length of time of between 2 min and 60 min, including 20 min, and optionally resuspending and repeating the centrifuging once, twice, or more, thereby resulting in a third supernatant and a third pellet, the third pellet including the desired fecal microbes; e) resuspending the third pellet in the presence of a cryoprotectant, thereby producing a refined suspension including the desired fecal microbes; f) freezing the refined suspension; and g) freeze-drying the frozen refined suspension, thereby providing the FMT. In some specific instances, the method can further optionally include: h) downstream processing the residue, the first supernatant, the second pellet, and/or the third supernatant, thereby producing a downstream product.

The fecal sample itself can be harvested from a single source or a variety of subjects and/or sources. The fecal sample can be harvested from a single region or a variety of regions.

In some cases, the fecal sample is harvested from an individual that is different than the subject to which the FMT will be administered.

The fecal sample can be mixed with other fecal samples at any stage throughout the method or divided into subsamples, whether before or after suspending and filtering, or the various filtrates, supernatants, pellets, and the like can be combined or divided to facilitate processing efficiency or quality.

In some cases, the fecal sample can be harvested from a donor that has a desirable diagnosis history with respect to one or more conditions. In some cases, the donor has a diagnosis history that shows a lack of autism spectrum disorder (ASD). In some cases, the donor is screened as not having ASD. In some cases, the donor is diagnosed as cognitively normal or cognitively above average.

In some cases, the fecal sample can be harvested from a donor on the basis of meeting a suitability threshold as determined from screening data, including medical background and health history. Some factors used to include or exclude fecal sample donors may include one or more of: obesity, a presence of beneficial fecal flora, childbirth type (e.g., vaginal delivery, C-section, etc.), having certain diseases or conditions (e.g., chronic infectious disease(s), known exposure to HIV or viral hepatitis, autoimmune disease(s), gastrointestinal disease or symptoms, atopic disease(s), metabolic disorders, mood disorders and neuroatypical, neurodegenerative disorder(s), chronic pain syndrome, malignancies, etc.), whether or not breastfed, activity/fitness level, donor age, diversity of diet, type of diet (e.g., omnivorous, carnivore, vegan, vegetarian, etc.), amount of lifetime use of certain agents (e.g., antibiotics, antifungals, antivirals, immune-suppressants, chemotherapy, etc.), allergy history, tobacco/*cannabis* smoking history including secondhand history, international travel, ADHD/ADD treatment, sleep issues (e.g. insomnia, frequent waking, nightmares), country of residence, various parameters related to blood and stool (e.g., presence of ova/parasites, viruses (including Multidrug-Resistant Organisms (MDROs): ESBL, MRSA, VRE), fungi (e.g., *C difficile* toxin B by PCR), and/or active infections (e.g., enteric pathogens)), or other serologic test results (e.g., Complete Blood Count (CBC) & Comprehensive Metabolic Panel (CMP), HIV (type 1 and 2), Hepatitis A virus IgM, Hepatitis B surface antigen, Hepatitis C virus antibody, *Treponema pallidum* (Cascade with reflex to RPR)).

In some cases, the fecal sample is held in quarantine for a period of time (e.g., 30 days, 60 days, 90 days, 120 days, or the like) to ensure all blood and stool screening passes any set standards or criteria.

In some cases, the fecal sample is included or excluded on the basis of a criteria. For example, the fecal sample one criteria may be its Type as based on a Bristol stool chart or other classification scale. In another example, the criteria may be exhibition of a selected pH or pH ranges of the fecal sample. In another example, the criteria may be the presence or absence of blood or mucus. It should be understood that the step of applying criteria for inclusion or exclusion may precede any of the processing steps described herein.

Suspending the fecal sample can be performed according to techniques understood in the art, including but not limited to aggressive mixing, vortexing, bag mixing, and the like. Without wishing to be bound by any particular theory, it is believed that skilled artisans will recognize that suspending a fecal sample broadly relates to techniques for reducing particle size and making fecal matter into a liquid composition having suspended fecal particulates. In some cases, suspension proceeds until a homogenous solution is achieved.

Filtering a fecal sample can be performed according to techniques understood in the art, including but not limited to, conventional filtration, suction filtration, bag filtration, and the like. Without wishing to be bound by any particular theory, it is believed that skilled artisans will recognize that filtering a fecal sample broadly relates to techniques for removing larger particulate matter from a fecal sample.

The filtering can be performed with a particle size cutoff that allows the desired fecal microbes to be adequately separated from larger pieces of fecal matter, as would be appreciated by a skilled artisan. In general, the filtering has a particle size cutoff of 150 microns, 200 microns, 250 microns, 300 microns, 350 microns, or 400 microns. In some cases, the filtering has a particle size cutoff of 400 microns. In some cases, the filtering has a particle size cutoff of 250 microns. In some cases, the filtering has a particle size cutoff of 150 microns. In some cases, the filtering involves filtering products out that are larger than 250 microns and keeping everything sized under 250 microns. In some cases, the filtering involves filtering products out that are larger than 150 microns. In some cases, the filtering involves filtering products out that are larger than 400 microns. Filtering may proceed with a limit on heat and oxygen exposure for the material to be filtered and filtered material. For example, filtering may proceed at a temperature between 1° C. and 10° C. In some cases, filtering may proceed at a temperature between 3° C. and 5° C. filtering may proceed at a temperature of 4° C.

The various centrifugation steps are performed under generally conventional conditions using generally conventional instrumentation. The inventor surprisingly discovered that the sequencing and control of different centrifugation steps can provide exceptional performance quality. It is understood that any of the centrifugation steps described herein may be performed on any volume of filtrate, such as volumes suitable for the available centrifugation instrumentation.

Following the suspending and filtering, the filtrate is centrifuged (also referred to herein as a first centrifugation or the centrifugation of step b)) at a first gravitational force for a first centrifugation length of time. Centrifuging the filtrate results in a first pellet and a first supernatant. The desired fecal microbes are contained in the first pellet. The centrifuging can optionally include one, two, three, four, five, or more resuspensions with fresh saline (or other suspending liquid) and decantings of supernatants.

To be clear and for the avoidance of doubt, the present disclosure covers: i) situations where the first centrifugation involves only a single centrifugation step that results in a first supernatant; ii) situations where the first centrifugation involves a first instance of centrifugation, after which the supernatant is gathered, the pellet is resuspended, and a second instance of centrifugation is performed with the same and/or similar operational parameters—the supernatant from the first instance can be combined with the supernatant from the second instance to define the "first supernatant" as a whole or the first supernatant may be only the supernatant from the first instance of centrifugation; iii) situations where the first centrifugation involves a first instance of centrifugation, after which the supernatant is gathered, the pellet is resuspended, and multiple subsequent instances of centrifugation, decanting, and resuspension are performed with the same and/or similar operational parameters—the supernatant from the first instance can be combined with the multiple supernatants from the multiple subsequent instances to define the "first supernatant" as a whole or the first supernatant may be only the supernatant from the first instance of centrifugation; iv) slight variations in centrifugation parameters (e.g. plus or minus 10%), while still being considered part of the "same" first centrifugation.

In some cases, the first centrifugation includes two resuspensions and decantings. In some cases, a total first centrifugation time of the first centrifugation of step b) can be between 6 min and 180 min, including 60 min.

The specific operational parameters of the first centrifugation step can be tailored for desired performance, including for the selection and/or exclusion of certain constituents. This disclosure expressly contemplates an active selection step in the methods disclosed herein, where the particular parameters of the first centrifugation are selected to provide a specific desired result in one or more of the output compositions.

In general, the first gravitational force is between 6000×g and 10,000×g, between 7000×g and 9000×g, or between 7500×g and 8500×g, including 8000×g. In general, the first centrifugation length of time is between 2 min and 60 min, between 5 min and 50 min, between 10 min and 45 min, between 15 min and 30 min, or between 15 min and 25 min, including 20 min.

In certain cases, the first gravitational force is between 6000×g and 10,000×g, including 8000×g. In certain cases, the first gravitational force is between 7000×g and 9000×g, including 8000×g. In certain cases, the first gravitational force is between 7500×g and 8500×g, including 8000×g. In certain cases, the first length of time is between 2 min and 60 min, including 20 min. In certain cases, the first length of time is between 10 min and 30 min, including 20 min. In certain cases, the first length of time is between 15 min and 25 min, including 20 min. In certain cases, the first gravitational force is between 6000×g and 10,000×g, including 8000×g, and the first length of time is between 2 min and 60 min, including 20 min. In certain cases, the first gravitational force is between 7000×g and 9000×g, including 8000×g, and the first length of time is between 10 min and 30 min, including 20 min. In certain cases, the first gravitational force is between 7500×g and 8500×g, including 8000×g, and the first length of time is between 15 min and 25 min, including 20 min.

Following the first centrifugation of step b), the first pellet is resuspended and centrifuged (also referred to herein as a second centrifugation or the centrifugation of step c)) at a second gravitational force for a second centrifugation length of time. The result is a second pellet and a second supernatant. The desired fecal microbes are contained in the second supernatant.

As discussed above with the first centrifugation of step b), the second centrifugation of step c) can be repeated multiple times, but with a slight modification due to the second supernatant being retained (along with the desired fecal microbes) rather than the first pellet. It should be appreciated that the centrifugation can be repeated zero, one, two, three, four, five, or more times, gathering and/or discarding the pellet each time and optionally adding additional liquid to maintain original volume. In some cases, the centrifugation is repeated twice. In some cases, a total second centrifugation time of the second centrifugation of step c) can be between 6 min and 180 min, including 60 min.

The specific operational parameters of the second centrifugation step can be tailored for desired performance, including for the selection and/or exclusion of certain constituents. This disclosure expressly contemplates an active selection step in the methods disclosed herein, where the particular parameters of the second centrifugation are selected to provide a specific desired result in one or more of the output compositions.

In general, the second gravitational force is between 250×g and 2000×g, between 500×g and 1500×g, or between 750×g and 1250×g, including 1000×g. In general, the second centrifugation length of time is between 2 min and 60 min, between 5 min and 50 min, between 10 min and 45 min, between 15 min and 30 min, or between 15 min and 25 min, including 20 min.

In certain cases, the second gravitational force is between 250×g and 2000×g, including 1000×g. In certain cases, the second gravitational force is between 500×g and 1500×g, including 1000×g. In certain cases, the second gravitational force is between 750×g and 1250×g, including 1000×g. In certain cases, the second length of time is between 2 min and 60 min, including 20 min. In certain cases, the second length of time is between 10 min and 30 min, including 20 min. In certain cases, the second length of time is between 15 min and 25 min, including 20 min. In certain cases, the second gravitational force is between 250×g and 2000×g, including 1000×g, and the second length of time is between 2 min and 60 min, including 20 min. In certain cases, the second gravitational force is between 500×g and 1500×g, including 1000×g, and the second length of time is between 10 min and 30 min, including 20 min. In certain cases, the second gravitational force is between 750×g and 1250×g, including 1000×g, and the second length of time is between 15 min and 25 min, including 20 min.

Following the second centrifugation of step c), the second supernatant or a dilution of the second supernatant is centrifuged (also referred to herein as a third centrifugation or the centrifugation of step d)) at a third gravitational force for a third centrifugation length of time. The result is a third pellet and a third supernatant. The desired fecal microbes are contained in the third pellet.

As discussed above with the first centrifugation of step b), the third centrifugation of step d) can be repeated multiple times, but with a slight modification due to the third supernatant being retained (along with the desired fecal microbes) rather than the first pellet. It should be appreciated that the centrifugation can be repeated zero, one, two, three, four, five, or more times, gathering and/or discarding the pellet each time and optionally adding additional liquid to maintain original volume. In some cases, the third centrifugation is repeated twice. In some cases, the third centrifugation is not repeated in step d). In some cases, a total third centrifugation time of the third centrifugation of step d) can be between 2 min and 180 min, including 20 min.

The specific operational parameters of the third centrifugation step can be tailored for desired performance, including for the selection and/or exclusion of certain constituents. This disclosure expressly contemplates an active selection step in the methods disclosed herein, where the particular parameters of the third centrifugation are selected to provide a specific desired result in one or more of the output compositions.

In general, the third gravitational force is between 6000×g and 10,000×g, between 7000×g and 9000×g, or between 7500×g and 8500×g, including 8000×g. In general, the third centrifugation length of time is between 2 min and 60 min, between 5 min and 50 min, between 10 min and 45 min, between 15 min and 30 min, or between 15 min and 25 min, including 20 min.

In certain cases, the third gravitational force is between 6000×g and 10,000×g, including 8000×g. In certain cases, the third gravitational force is between 7000×g and 9000×g, including 8000×g. In certain cases, the third gravitational force is between 7500×g and 8500×g, including 8000×g. In certain cases, the third length of time is between 2 min and 60 min, including 20 min. In certain cases, the third length of time is between 10 min and 30 min, including 20 min. In certain cases, the third length of time is between 15 min and 25 min, including 20 min. In certain cases, the third gravitational force is between 6000×g and 10,000×g, including 8000×g, and the third length of time is between 2 min and 60 min, including 20 min. In certain cases, the third gravitational force is between 7000×g and 9000×g, including 8000×g, and the third length of time is between 10 min and 30 min, including 20 min. In certain cases, the third gravitational force is between 7500×g and 8500×g, including 8000×g, and the third length of time is between 15 min and 25 min, including 20 min.

Following the third centrifugation of step d), the third pellet is resuspended in the presence of a cryoprotectant, thereby producing a refined suspension. The refined suspension includes the desired fecal microbes.

The cryoprotectant can be one or more of the cryoprotectants articulated above. In some cases, the cryoprotectant is D-(+)Trehalose dihydrate. The cryoprotectant can be added in an amount that results in the FMT containing between 0.1% and 20% by weight of the cryoprotectant, including 5% by weight.

The cryoprotectant can be added at effectively any point in the method, so long as the subsequent processing steps would not lead to its removal. While the cryoprotectant may most conventionally be added during step e), it is contemplated for the cryoprotectant to be added at other times. The cryoprotectant can be added to the first pellet prior to or during step c) or to the resuspended first pellet during step c); the cryoprotectant can be added to the second supernatant prior to or during step d) or to the optionally diluted second supernatant during step d); and/or the cryoprotectant can be added to the third pellet prior to or during step e) or to the resuspended third pellet during step e). In some cases, the cryoprotectant is added prior to step e). In some cases, the cryoprotectant is added during step e).

Following the resuspension, the refined suspension is frozen.

Following the freezing of the refined suspension, the frozen refined suspension is freeze-dried, resulting in the FMT. Freeze-drying may take place over a number of days, such as at least 6 days, at least 5 days, at least 4 days, at least 2 days, or at least 1 day.

The inventors surprisingly discovered that the method retains a high percentage of the desired fecal microbes from the original fecal sample. In other words, the inventors unexpectedly discovered that the method disclosed herein has a high survival rate for the desired fecal microbes, given that the degree to which the odor and flavor have been eliminated is most typically associated with harsh treatments that require the killing of all or most living things, including desirable fecal microbes. In some cases, at least 95% of the desired fecal microbes that are present in the fecal matter is retained in the FMT following the method. In some cases, at least 75% of the desired fecal microbes that are present in the fecal matter is retained in the FMT following the method. In some cases, at least 50% of the desired fecal microbes that are present in the fecal matter is retained in the FMT following the method. In some cases, the count of desired fecal microbes present in the fecal matter or FMT is determined by flow cytometry.

The inventors were able to achieve an unexpectedly strong probiotic count in the FMT. Unless the context clearly dictates otherwise, all total probiotic counts described herein refer to a probiotic count of desired fecal microbes. In some cases, the FMT has a total probiotic count of at least 50 billion colony forming units (CFUs) following the method. In some cases, the FMT has a total probiotic count of at least 10 billion CFUs following the method. In some cases, the FMT has a total probiotic count of at least 1 billion CFUs following the method. In some cases, the probiotic count of desired fecal microbes is determined by flow cytometry.

One of the two truly landmark achievements of the present disclosure is that the FMT produced by the methods described herein is odorless to a significant portion of the population. As measured by a triangular comparison test, such as the one described in ISO 4120 (ISO 4120:2021, Sensory analysis Methodology Triangle test), which is hereby incorporated by reference in its entirety, the FMT has an odor as evaluated with a confidence of 95% to be odorless for more than 70% of the population. In some cases, the FMT has an odor as evaluated with a confidence of 95% to be odorless for more than 60% of the population. In some cases, the FMT has an odor as evaluated with a confidence of 95% to be odorless for more than 50% of the population.

The other of the truly landmark achievements of the present disclosure is that the FMT produced by the methods described herein is tasteless to a significant portion of the population. As measured by a triangular comparison test, such as the one described in ISO 4120, the FMT has a flavor as evaluated with a confidence of 80% to be flavorless for more than 70% of the population. In some cases, the FMT has a flavor as evaluated with a confidence of 80% to be flavorless for more than 60% of the population. In some cases, the FMT has a flavor as evaluated with a confidence of 80% to be flavorless for more than 50% of the population.

Without wishing to be bound by any particular theory, and despite having test results that indicate some degree of retention of color, the FMT is a very low color powder and/or produces a very low color liquid when dissolved.

In some cases, the compositions described herein can be process and handled in one environment, sealed within that environment, transported to a different environment for centrifugation, and then either returned to the first environment or taken to a third, different environment. This approach enables the use of a clean environment for processing the samples and a non-sterile environment for the centrifugation.

The FMT is stable when stored under a variety of conditions, as measured by one or more of a retention of a desired activity level, a viability, an engraftment, or an efficacy of the gut microbiome over time during storage. In some aspects, the FMT may be considered shelf-stable. In general, storing the FMT under predetermined storage conditions for a predetermined length of time retains the desired activity level.

The predetermined storage conditions can be −80° C. to 4° C. The predetermined storage conditions can be −20° C. to 0° C. The predetermined storage conditions can be 0° C. to 4° C. The predetermined storage conditions can be room temperature. It should be understood that room temperature describes a temperature of an ambient environment, such as a temperature between about 68° F. to 75° F., including 70° F. The predetermined storage time can be more than 2 years, including more than 5 years. The predetermined storage time can be 2 years. The predetermined storage time can be 1 year. The predetermined storage time can be between 3 months and 5 years. The predetermined storage time can be 6 months. The predetermined storage time can be 3 months. The desired activity level can be 100%. The desired activity level can be 85%. The desired activity level can be 70%.

The method can optionally further include: h) downstream processing the residue, the first supernatant, the second pellet, and/or the third supernatant, thereby producing a downstream product.

Downstream processing the residue can include autoclaving the residue.

Downstream processing the first supernatant can include concentrating the first supernatant, dehydrating the first supernatant, freeze-drying the first supernatant, or a combination thereof. The decanted supernatant(s) from the first centrifugation of step b) is the first supernatant and optionally includes the supernatants from resuspensions in the instances where they occur. The decanted supernatants can be kept separate or combined.

Downstream processing the second pellet can include autoclaving and/or suspending the second pellet.

Downstream processing the third supernatant includes concentrating the third supernatant, dehydrating the third supernatant, freeze-drying the third supernatant, or a combination thereof.

Given that the desired fecal microbes are the entity that is being transplanted, and given that the residue, the first supernatant, the second pellet, and the third supernatant substantially lack the desired fecal microbes, they all could conventionally be viewed as waste streams, but the inventors surprisingly discovered that the residue, the first supernatant, the second pellet, and/or the third supernatant could be further processed for useful purposes, thereby enhancing the overall efficiency of the process.

The method disclosed herein can be fully automated, as would be appreciated by an industrial automation engineer.

The steps of extracting desirable microbes may be performed in a short duration of time. For example, the overall process of extracting microbes may be performed in less than four hours, less than three hours, less than two hours, or less than 90 minutes.

In an aspect, the present disclosure provides a therapeutic composition for oral administration to a subject. The therapeutic composition can include the FMT or the powder described herein. In addition, the therapeutic composition can include a pharmaceutically acceptable carrier. Though one of the principal advantages of the present composition is the ability to be used without additional additives, the presence of such additives are still expressly contemplated within the scope of the invention. One example of a suitable additive for use with the compositions described herein is an enteric coating that is tailored to enhance survivability of the desirable fecal microbes as they navigate the subject's GI tract.

Figure 4:
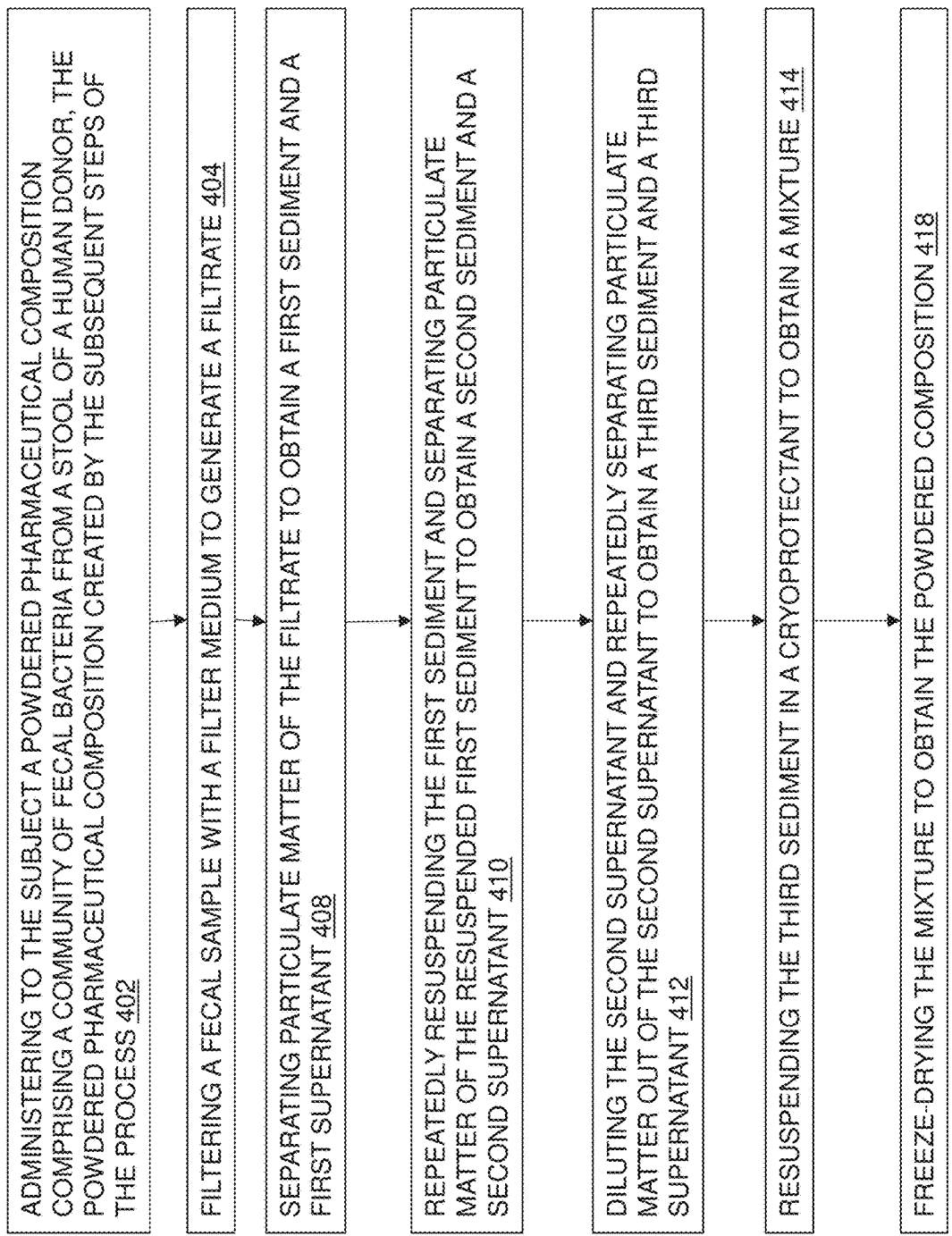
FIG. 4 depicts a procedure for treating a disorder with an FMT composition.

Products produced by any of the processes described herein may be useful in the treatment of a number of disorders, such as autism spectrum disorder (ASD), a gastrointestinal symptom associated with ASD, colitis, Crohn's, Parkinson's, Alzheimer's, post-cancer, chronic digestive issues, gastrointestinal issues, or any condition being studied or approved for treatment via microbial transfer. In an embodiment, and referring to FIG. 4, an example procedure 400 for treating an autism spectrum disorder (ASD) or a gastrointestinal symptom associated with ASD in a subject in need thereof may include an operation 402 of administering to the subject a powdered pharmaceutical composition, such as an amount of a pharmaceutical composition effective for treating said ASD, comprising a community of fecal bacteria from a stool of a human donor, the powdered pharmaceutical composition created by a process of the subsequent steps of the procedure 400, including an operation 404 of filtering a fecal sample with a filter medium to generate a filtrate, an operation 408 of separating particulate matter of the filtrate to obtain a first sediment and a first supernatant, an operation 410 of repeatedly resuspending the first sediment and separating particulate matter of the resuspended first sediment to obtain a second sediment and a second supernatant, an operation 412 of diluting the second supernatant and repeatedly separating particulate matter out of the second supernatant to obtain a third sediment and a third supernatant, an operation 414 of resuspending the third sediment in a cryoprotectant to obtain a mixture, and an operation 418 of freeze-drying the mixture to obtain a freeze-dried composition that is powdered, wherein the powdered composition may be substantially tasteless, odorless, and colorless. The procedure 400 may include administering a loading dose initially, followed by maintenance doses, or extended treatment, over a time period. In embodiments, the loading dose and the maintenance dose may be prepared via the same procedures. In embodiments, and as previously described herein, any powdered compositions derived from freeze-drying any of the first supernatant, the second supernatant, the third supernatant, the first sediment, the second sediment, or the third sediment may be useful in the procedure and may be administered as the loading dose and/or the maintenance dose. Similarly, any of the first supernatant, the second supernatant, the third supernatant, the first sediment, the second sediment, or the third sediment may be discarded.

Figure 5:
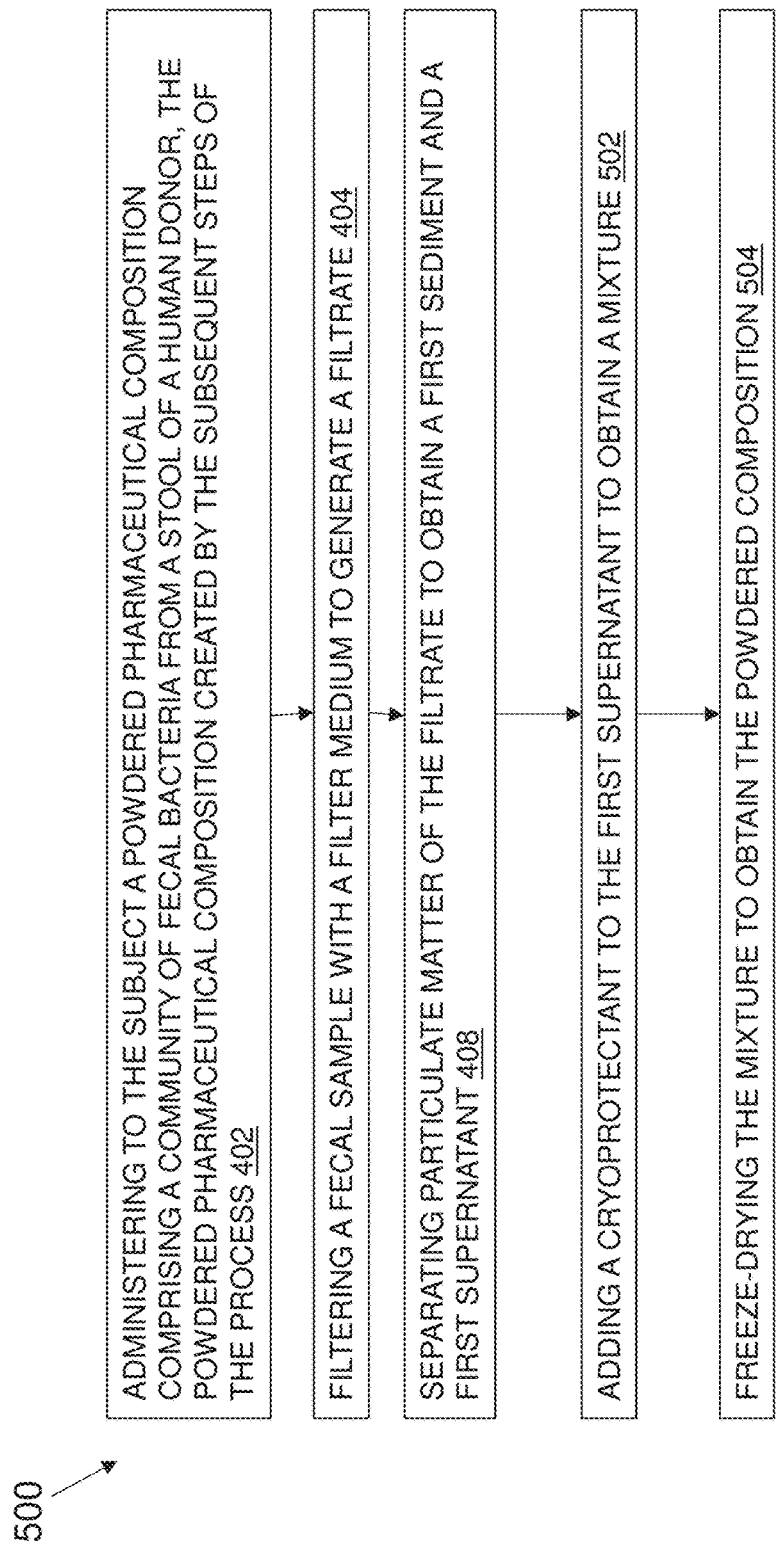
FIG. 5 depicts a procedure for treating a disorder with an FMT composition.

For example, and referring to FIG. 5, a procedure 500 for treating an autism spectrum disorder (ASD) or a gastrointestinal symptom associated with ASD in a subject in need thereof may include an operation 402 of administering to the subject a powdered pharmaceutical composition comprising a community of fecal bacteria from a stool of a human donor, the powdered pharmaceutical composition created by subsequent steps of the procedure 500, including an operation 404 of filtering a fecal sample with a filter medium to generate a filtrate, an operation 408 of separating particulate matter of the filtrate to obtain a first sediment and a first supernatant, an operation 502 of adding a cryoprotectant to the first supernatant to obtain a mixture, and an operation 504 of freeze-drying the mixture to obtain a freeze-dried, powdered, wherein the powdered composition may be substantially tasteless, odorless, and colorless.

In an embodiment, the loading dose may be a bolus dose on day one, and a bolus dose on day two. In the example, the bolus doses may be the same or different. In an example of an encapsulated powdered composition, the bolus dose may be at least 10 capsules, at least 20 capsules, at least 30 capsules, or at least 35 capsules. In an example of a non-encapsulated product, the bolus dose may be at least 10 vials, at least 20 vials, at least 30 vials, or at least 35 vials. The maintenance dose may be a fraction of the bolus dose and may be administered daily for a pre-defined number of weeks, such as four weeks, eight weeks, sixteen weeks, or the like, or for other durations such as months (e.g., 6 months, 9 months, etc.) or years (e.g., 1 year, 2 years, 5 years, etc.). In some aspects, the maintenance dose schedule may be a periodic one. In some cases, after a set amount of time on a prophylactic basis or to address reoccurring symptoms, the maintenance dose may be re-initiated. For example, a 4 week treatment may be delivered every 6 months.

In some embodiments, the loading dose may be delivered via an enema. In some embodiments, the human donor is the subject. It should be understood that the dose and/or duration of dosing of the powdered composition may be variable or customized based on any number of factors, such as size, weight, age, severity of disease or symptoms, tolerance levels, diet, ability to swallow, prior treatment, additional treatments/supplements, comorbidities, or the like. For example, a dose may vary in accordance with a current or desired rating on at least one of the Childhood Autism Rating Scale (CARS), the Childhood Autism Rating Scale 2-Standard Form (CARS2-ST), or the Childhood Autism Rating Scale 2-High Functioning (CARS2-HIF). In another example, the powdered composition may be complemented by a specific diet and/or concomitant pharmacological treatment, and the dose or duration of dosing may vary depending on aspects of the diet and/or concomitant pharmacological treatment.

In embodiments, treating subjects with an autism spectrum disorder (ASD) or a gastrointestinal symptom associated with ASD using the powdered compositions described herein may result in the subject exhibiting a reduction in ASD symptom severity after the administering as compared to before the administering. For example, an assessment may be administered to the subject prior to administering treatment, such as an assessment system selected from a group consisting of Childhood Autism Rating Scale (CARS), Childhood Autism Rating Scale 2-Standard Form (CARS2-ST), Childhood Autism Rating Scale 2-High Functioning (CARS2-HIF), Autism Treatment Evaluation Checklist (ATEC)), Gastrointestinal symptoms (Gastrointestinal Symptom Rating Scale (GSRS)), Bristol scale, quality of life (Quality of Life in Autism Questionnaire (QoLA)), or another known or not-yet-known assessment. After a duration of treatment comprising administering one or more doses of the powdered composition, the selected assessment may be re-administered to determine if there has been an improvement in any of the administered assessments or a reduction in severity of observed symptoms. For example, re-assessment may take place at 30 days post-treatment, 60 days post-treatment, 90 days post-treatment, 120 days post-treatment, or 180 days post-treatment. Additionally, a number of subjective measures may be assessed, such as parents' view on change, change in medication/supplements/diet/overall health/stool, or the like. For example, an amount of a pharmaceutical composition effective for treating an ASD may be an amount that results in a 10% reduction in severity of ASD symptoms, such as determined by the selected assessment system. In embodiments, the effective amount may be delivered in a loading dose, or may be delivered in a combination of a loading and one or more maintenance doses.

In embodiments, a long-term maintenance dose may also be administered after completing the loading dose and/or maintenance doses. In some embodiments, the loading and maintenance doses together may be considered FMT, while the long-term maintenance may be considered post-FMT maintenance. Post-FMT maintenance may be dosed hourly, daily, weekly, monthly, or the like. Post-FMT maintenance doses may be derived from any of the processes described herein. Post-FMT maintenance doses may be based on metabolome products, such as supernatant-derived compositions, or compositions derived from autoclaved fecal samples, for example.

In embodiments, either of the procedure 400 or procedure 500, and related process steps described herein, as well as any of the powdered compositions described herein, may also be useful in the treatment of a subject with *C. difficile* infection, colitis, Crohn's, cancer, post-cancer, chronic digestive issues, gastrointestinal issues (such as those associated with long Covid or other viral disease), inflammatory bowel disease (IBD), inflammatory bowel syndrome (IBS), metabolic disorders (i.e. type 2 diabetes, insulin resistance, metabolic syndrome), Alzheimer's Disease, Parkinson's disease, age-related changes (i.e. cognition, frailty, mood), anti-aging multiple sclerosis neuropsychiatric conditions (i.e. anxiety, depression), or any condition being studied or approved for treatment via microbial transfer. It should be understood that the dose of the powdered composition may be variable or customized based on any number of factors, such as size, weight, age, disease or disorder being treated, severity of disease or symptoms, tolerance levels, ability to swallow, prior treatment, or the like.

Figure 6:
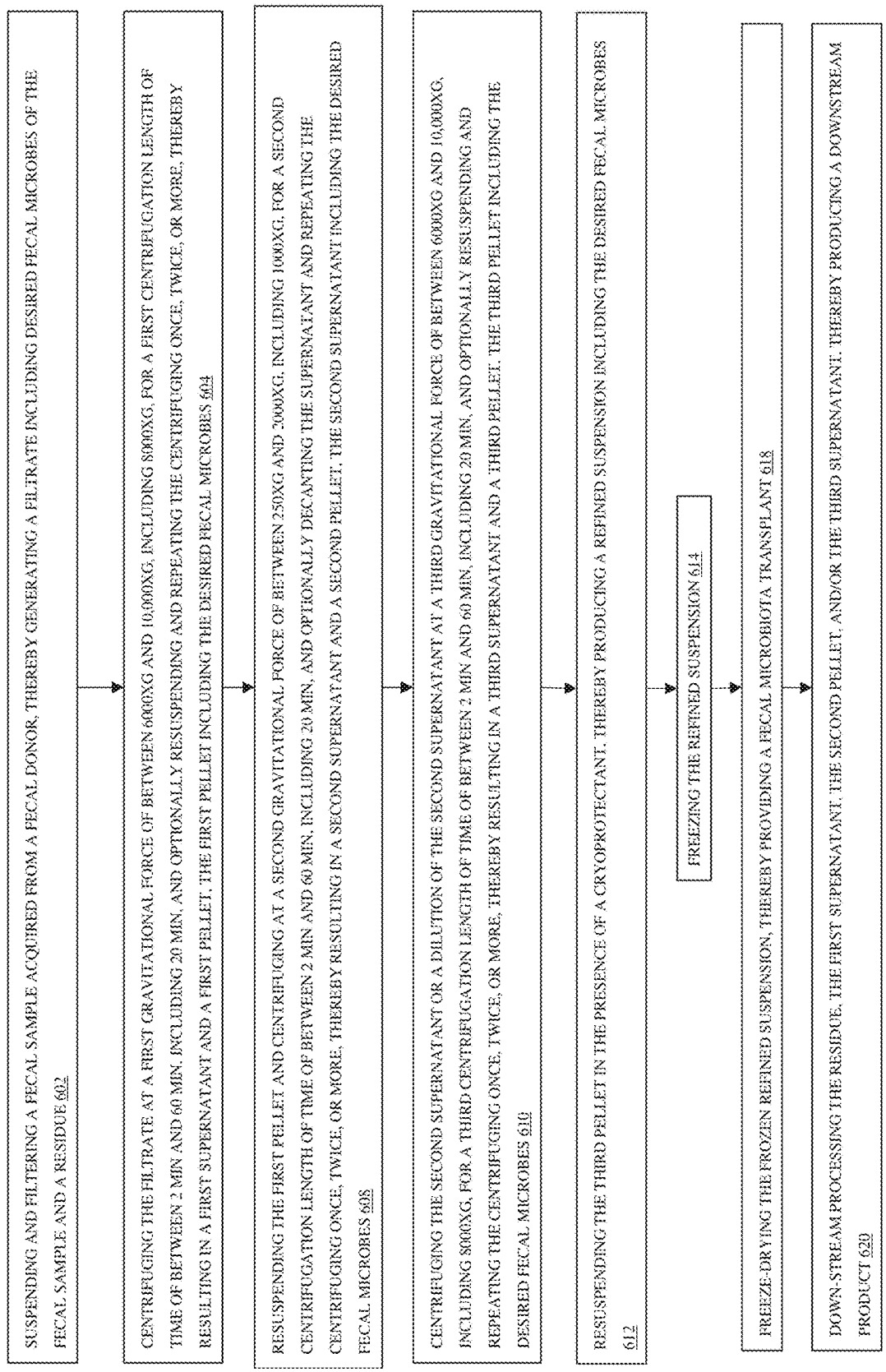
FIG. 6 depicts a procedure for preparing an FMT composition.

Referring now to FIG. 6, a method 600 of dividing human fecal matter into useful output products, including at least one fecal microbiota transplant (FMT) having palatable odor and flavor may include a step 602 of suspending and filtering a fecal sample acquired from a fecal donor, thereby generating a filtrate including desired fecal microbes of the fecal sample and a residue. The method 600 may further include a step 604 of centrifuging the filtrate at a first gravitational force of between 6000×g and 10,000×g, including 8000×g, for a first centrifugation length of time of between 2 min and 60 min, including 20 min, and optionally resuspending and repeating the centrifuging once, twice, or more, thereby resulting in a first supernatant and a first pellet, the first pellet including the desired fecal microbes. The method may further include a step 608 of resuspending the first pellet and centrifuging at a second gravitational force of between 250×g and 2000×g, including 1000×g, for a second centrifugation length of time of between 2 min and 60 min, including 20 min, and optionally decanting the supernatant and repeating the centrifuging once, twice, or more, thereby resulting in a second supernatant and a second pellet, the second supernatant including the desired fecal microbes. The method may further include a step 610 of centrifuging the second supernatant or a dilution of the second supernatant at a third gravitational force of between 6000×g and 10,000×g, including 8000×g, for a third centrifugation length of time of between 2 min and 60 min, including 20 min, and optionally resuspending and repeating the centrifuging once, twice, or more, thereby resulting in a third supernatant and a third pellet, the third pellet including the desired fecal microbes. The method may further include a step 612 of resuspending the third pellet in the presence of a cryoprotectant, thereby producing a refined suspension including the desired fecal microbes. The method may further include a step 614 of freezing the refined suspension and a step of 618 of freeze-drying the frozen refined suspension, thereby providing a fecal microbiota transplant. The method 600 may optionally include a step 620 of down-stream processing the residue, the first supernatant, the second pellet, and/or the third supernatant, thereby producing a downstream product.

Referring now to FIG. 7, a method 700 of treating a subject having been diagnosed with autism spectrum disorder (ASD) may include administering a predetermined loading dose for a fecal microbiota transplant (FMT) composition under a loading dose protocol 702, and administering a predetermined maintenance dose of the FMT under a maintenance dose protocol 704. In certain embodiments, either the loading dose protocol or the maintenance dose protocol requires orally administering 50 billion CFUs.

Referring now to FIG. 8, an embodiment of a system 800 for producing FMT having palatable odor and flavor is depicted. The system 800 may include a filtration system 802, such as a BagMixer, into which a container 804, such as a bag, is placed to mix a suspended fecal sample and filter the suspension to obtain a filtrate, which is placed into a container 810 for subsequent processing. The filtrate is separated, such as in a centrifuge 808, to obtain supernatant and sediment/pellet, either of which may be useful for further downstream processing. In embodiments, where the sediment/pellet is used, it may be resuspended in fresh solvent, such as by use of a vortex machine, shaker, or the like. In embodiments, if the supernatant is used, it may be decanted and optionally diluted for further processing. Products obtained after any of the steps of filtration, dilution, centrifugation, mixing, decanting, and/or resuspension may be mixed with a cryoprotectant, frozen, such as in a freezer 812, and freeze-dried, such as in a freeze dryer 814, thereby providing the FMT.

FIG. 9 is a flowchart of an example method 900 for dividing human fecal matter into useful output products, including at least one fecal microbiota transplant (FMT) having palatable odor and flavor. At step 902, the method 900 involves suspending a fecal sample acquired from a fecal donor in a first volume. At step 904, the method 900 involves filtering the suspended fecal sample thereby generating a filtrate including desired fecal microbes of the fecal sample. At step 908, the method 900 involves centrifuging the filtrate at a first gravitational force of 8000×g for a first centrifugation length of time of 20 min, retaining a first sediment, and discarding a first supernatant. At step 910, the method 900 involves adding fresh solvent, resuspending the first sediment, and centrifuging each container at the first gravitational force for the first centrifugation length of time, retaining a second sediment, and discarding a second supernatant. At step 912, the method 900 involves adding fresh solvent, resuspending the second sediment, and centrifuging the first gravitational force for the first centrifugation length of time, retaining a third sediment, and discarding a third supernatant from each of the separate containers. At step 914, the method 900 involves adding fresh solvent, resuspending the third sediment, and centrifuging at a second gravitational force of 1000×g for a second centrifugation length of time of 20 min, retaining a fourth supernatant, and discarding a fourth sediment. At step 918, the method 900 involves centrifuging the fourth supernatant or a dilution thereof at the second gravitational force for the second centrifugation length of time, retaining a fifth supernatant, and discarding a fifth sediment. At step 920, the method 900 involves centrifuging the fifth supernatant or a dilution thereof at the second gravitational force for the second centrifugation length of time, retaining a sixth supernatant, and discarding a sixth sediment. At step 922, the method 900 involves centrifuging the sixth supernatant or a dilution thereof at the first gravitational force for the first centrifugation length of time, discarding a seventh supernatant, and obtaining a seventh sediment. At step 924, the method 900 involves resuspending the seventh sediment in the presence of a cryoprotectant, thereby producing a refined suspension. At step 928, the method 900 involves freezing the refined suspension. At step 930, the method 900 involves and freeze-drying the frozen refined suspension, thereby providing the FMT.

It should be understood that powdered compositions derived from any supernatant (e.g., first, second, or third), or any sediment (e.g., first, second, or third) may be substantially tasteless, odorless, and colorless. In some embodiments, powdered compositions derived from any supernatant (e.g., first, second, or third), or any sediment (e.g., first, second, or third) may not be substantially tasteless, odorless, and colorless. In some embodiments, powdered compositions derived from any fecal samples that have been autoclaved may not be substantially tasteless, odorless, and colorless. For example, a first supernatant that is freeze-dried into a powder may not be substantially tasteless, odorless, and colorless and may be encapsulated.

The methods and systems described herein may transform physical and/or intangible items from one state to another. The methods and systems described herein may also transform data representing physical and/or intangible items from one state to another.

The elements described and depicted herein, including in flow charts, block diagrams, and/or operational descriptions, depict and/or describe specific example arrangements of elements for purposes of illustration. However, the depicted and/or described elements, the functions thereof, and/or arrangements of these, may be implemented on machines, such as through computer executable transitory and/or non-transitory media having a processor capable of executing program instructions stored thereon, and/or as logical circuits or hardware arrangements. Example arrangements of programming instructions include at least: monolithic structure of instructions; standalone modules of instructions for elements or portions thereof, and/or as modules of instructions that employ external routines, code, services, and so forth; and/or any combination of these, and all such implementations are contemplated to be within the scope of embodiments of the present disclosure Examples of such machines include, without limitation, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipment, servers, routers and the like. Furthermore, the elements described and/or depicted herein, and/or any other logical components, may be implemented on a machine capable of executing program instructions. Thus, while the foregoing flow charts, block diagrams, and/or operational descriptions set forth functional aspects of the disclosed systems, any arrangement of program instructions implementing these functional aspects are contemplated herein. Similarly, it will be appreciated that the various steps identified and described above may be varied, and that the order of steps may be adapted to particular applications of the techniques disclosed herein. Additionally, any steps or operations may be divided and/or combined in any manner providing similar functionality to the described operations. All such variations and modifications are contemplated in the present disclosure. The methods and/or processes described above, and steps thereof, may be implemented in hardware, program code, instructions, and/or programs or any combination of hardware and methods, program code, instructions, and/or programs suitable for a particular application. Example hardware includes a dedicated computing device or specific computing device, a particular aspect or component of a specific computing device, and/or an arrangement of hardware components and/or logical circuits to perform one or more of the operations of a method and/or system. The processes may be implemented in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and computer readable instructions, or any other machine capable of executing program instructions.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or computer readable instructions described above. All such permutations and combinations are contemplated in embodiments of the present disclosure.

EXAMPLES

Some embodiments described herein are further illustrated by the following example which should not be construed as limiting, Example 1. Preparation of an FMT Composition To prepare an FMT composition, stool samples were evaluated for at least pH, stool type (e.g., stool type as identified from a Bristol chart), presence of a contaminant (e.g., blood, mucus, other), and color. Suitable samples, as determined by one or more of the intended condition(s) to treat, the intended subject(s) to treat, a regulatory policy, a practitioner's instruction, or the like, were further processed. 100 grams of stool sample was added to a BagPage filter bag, 400 ml of saline was added, and then the bag was placed in a BagMixer for 2 minutes. 50 ml of the filtered solution was withdrawn and transferred to a tube. The BagMixer was run again for 2 minutes and another 50 ml of filtered solution was withdrawn and placed in a tube. 100 ml of saline was added to the BagPage filter bag, the BagMixer was run again twice for 2 minutes each time, and 50 ml of filter solution was withdrawn after each time and placed in a tube. Another 100 ml of saline was added to the BagPage filter bag, the BagMixer was run again twice for 2 minutes each time, and 50 ml of filter solution was withdrawn after each time and placed in a tube. All six tubes with 50 ml each of filtered solution were placed in a centrifuge and run at 8000×g for 30 minutes at 4° C. The supernatant was discarded and each tube was filled to the 45 ml line with fresh saline and the settled material was resuspended using the vortex machine. Centrifugation, supernatant discarding, and resuspension were repeated twice.

After the third resuspension, the tubes were once again subjected to centrifugation at 1000×g for 20 min at 4° C. The supernatant was transferred to a clean tube and the volume was adjusted with a saline solution up to 45 ml. Centrifugation, supernatant transfer, and volume adjustment to 45 ml was repeated twice. After the third volume adjustment, the tubes were once again subjected to centrifugation at 8000×g for 20 min at 4° C. The supernatant was discarded. 32 ml of 5% D-(+)-Trehalose dihydrate was added to each tube and vortexed until the settled material was resuspended.

1.5 ml of the resuspended material was transferred into 1.5 ml vials and frozen at −80° C. overnight. The vial weights ranged between 60 and 140 mg. The frozen vials were removed from the freezer and freeze-dried for about three days with opened lids. The vials were sealed once complete.

The finished powder product was assessed for odor, flavor, and color using ISO 4120 standards, among other evaluative techniques, by an independent contracted third party.

In one batch of tests, the powder was diluted in 5 ounces of water and subjected to a triangular test. The triangular test operates by comparing two different samples, A and B. Each panelist in the test is given three samples, either two A samples and one B sample or one A sample and two B samples. Panelists are asked to identify which sample is different from the other two. The number of correct answers were counted and statistically analyzed under ISO 4120 standards to assess the degree to which individuals can taste, smell, or see a difference between the inventive composition and a control (tap water).

For the odor assessment, 11 of 30 panelists correctly identified the different sample. According to the ISO 4120 table of triangular test outcomes, we conclude with a confidence of 95% that the composition is odorless for more than 70% of the population.

For the taste assessment, 12 of 30 panelists correctly identified the different sample. According to the ISO 4120 table of triangular test outcomes, we conclude with a confidence of 80% that the product is tasteless for more than 70% of the population.

For the color assessment, 27 of 30 panelists correctly identified the different sample. While this is a subpar result in terms of showing colorlessness when compared with a control, human perception of color is highly skewed by the presence of a local comparison. We understand this intuitively based on a few common observations. As one example, optical illusions can be created by changing the surrounding color environment, so two identical colors and shades appear very different, despite being identical, due to environmental context. As another example, teeth whitening advertisements observe that the true lack of whiteness of teeth cannot be observed without comparison to a truer white, such as a tissue—this is quite literally the concept that we believe we are seeing here, where the control sample is the "white tissue", and where the test sample is the individual's teeth. If a panelist were to view the test sample in a vacuum without the comparison (e.g., to look in the mirror without a tissue for whiteness comparison), they may conclude that the composition is colorless. However, if they view the test sample next to a comparison (e.g., to use the tissue), they may show the results that we achieved.

While the disclosure has been disclosed in connection with the preferred embodiments shown and described in detail, various modifications and improvements thereon will become readily apparent to those skilled in the art. Accordingly, the spirit and scope of the present disclosure is not to be limited by the foregoing examples, but is to be understood in the broadest sense allowable by law.

What is claimed is:

1. A method of producing odorless and/or flavorless fecal microbiota transplant (FMT), the method comprising the following steps:
 a) suspending and filtering a fecal sample acquired from a fecal donor, thereby generating a filtrate including desired fecal microbes of the fecal sample and a residue;
 b) centrifuging the filtrate at a first gravitational force of between 6000×g and 10,000×g for a first centrifugation length of time of between 2 min and 60 min and optionally resuspending and repeating the centrifuging once, twice, or more, thereby resulting in a first supernatant and a first pellet, the first pellet including the desired fecal microbes;

c) resuspending the first pellet and centrifuging at a second gravitational force of between 250×g and 2000×g for a second centrifugation length of time of between 2 min and 60 min and optionally decanting the first supernatant and repeating the centrifuging once, twice, or more, thereby resulting in a second supernatant and a second pellet, the second supernatant including the desired fecal microbes;

d) centrifuging the second supernatant or a dilution of the second supernatant at a third gravitational force of between 6000×g and 10,000×g for a third centrifugation length of time of between 2 min and 60 min and optionally resuspending and repeating the centrifuging once, twice, or more, thereby resulting in a third supernatant and a third pellet, the third pellet including the desired fecal microbes;

e) resuspending the third pellet in a presence of a cryoprotectant, thereby producing a refined suspension including the desired fecal microbes;

f) freezing the refined suspension; and g) freeze-drying the frozen refined suspension, thereby providing the FMT.

2. The method of claim 1, wherein the fecal donor is screened as not having autism spectrum disorder.

3. The method of claim 1, wherein the fecal donor is cognitively normal or cognitively above average.

4. The method of claim 1, wherein the filtering of step a) has a particle size cutoff of 400 microns.

5. The method of claim 1, the method further comprising, prior to step b), selecting the first gravitational force and/or the first centrifugation length of time.

6. The method of claim 1, the method further comprising, prior to step b), selecting the second gravitational force and/or the second centrifugation length of time.

7. The method of claim 1, wherein the first gravitational force is between 7500×g and 8500×g.

8. The method of claim 1, wherein the first centrifugation length of time is between 15 min and 30 min.

9. The method of claim 1, wherein step b) includes resuspending and repeating the centrifuging two times.

10. The method of claim 1, wherein the second gravitational force is between 750×g and 1250×g.

11. The method of claim 1, wherein the second centrifugation length of time is between 15 min and 30 min.

12. The method of claim 1, wherein step c) includes decanting the first supernatant and repeating the centrifugation twice.

13. The method of claim 1, wherein the FMT has an odor as evaluated with a confidence of 95% to be odorless for more than 50% of a population using a triangular test.

14. The method of claim 1, wherein the FMT has a flavor as evaluated with a confidence of 80% to be flavorless for more than 50% of a population using a triangular test.

15. The method of claim 1, further comprising storing the FMT under predetermined storage conditions for a predetermined storage length of time, wherein the FMT retains a desired activity level under predetermined storage conditions for the predetermined storage length of time, wherein the predetermined storage conditions are −80° C. to 4° C., the predetermined storage time is 1 year, and/or the desired activity level is 100%.

16. The method of claim 1, wherein at least 50% of the desired fecal microbes that are present in the fecal sample is retained in the FMT following the method.

17. The method of claim 1, wherein the FMT and the fecal sample have different colors.

18. An FMT made by the method of claim 1.

19. The method of claim 1, wherein the first gravitational force is between 7500xg and 8500xg, and the first centrifugation length of time is between 15 min and 30 min.

20. The method of claim 1, wherein the second gravitational force is between 750xg and 1250xg and the second centrifugation length of time is between 15 min and 30 min.

21. The method of claim 13, wherein the FMT has a flavor as evaluated with a confidence of 80% to be flavorless for more than 50% of the population using the triangular test.

22. The method of claim 1, wherein the first gravitational force is between 7500xg and 8500xg, the first centrifugation length of time is between 15 min and 25 min, the second gravitational force is between 750xg and 1250xg and the second centrifugation length of time is between 15 min and 20 min.

23. The method of claim 1, wherein the cryoprotectant is at least one of an amino acid, a simple sugar, dimethyl sulfoxide (DMSO), or glycerol.

24. The method of claim 1, wherein step b) includes resuspending and repeating the centrifuging once, twice, or more.

25. The method of claim 24, wherein step b) includes a total first centrifugation time of between 6 minutes and 180 minutes.

26. The method of claim 1, wherein step c) includes decanting the first supernatant and repeating the centrifugation once, twice, or more.

27. The method of claim 26, wherein step c) includes a total second centrifugation time of between 6 minutes and 180 minutes.

28. The method of claim 1, wherein step d) includes resuspending and repeating the centrifuging once, twice, or more.

29. The method of claim 28, wherein step d) includes a total third centrifugation time of between 2 minutes and 180 minutes.

30. The method of claim 1, further comprising storing the FMT under predetermined storage conditions for a predetermined storage length of time, wherein the FMT retains a desired activity level under predetermined storage conditions for the predetermined storage length of time, wherein the predetermined storage conditions are between 68° F. and 75°, the predetermined storage time is greater than 1 year, and the desired activity level is greater than 70%.

31. The method of claim 1, the method further comprising: h) downstream processing the residue, the first supernatant, the second pellet, and/or the third supernatant, thereby producing a downstream product.

32. The method of claim 1, wherein the method is automated.

33. The method of claim 1, wherein the FMT has an odor as evaluated with a confidence of 95% to be odorless for more than 70% of a population using a triangular test.

34. The method of claim 1, wherein the FMT has a flavor as evaluated with a confidence of 80% to be flavorless for more than 70% of a population using a triangular test.

35. The method of claim 1, wherein the first centrifugation is not repeated.

36. The method of claim 1, wherein the second centrifugation is not repeated.

37. The method of claim 1, wherein the third centrifugation is not repeated.

38. The method of claim 1, wherein the FMT has a total probiotic count of at least 1 billion CFUs.

* * * * *